(12) United States Patent
Wasserman et al.

(10) Patent No.: US 12,083,332 B2
(45) Date of Patent: Sep. 10, 2024

(54) CONNECTOR FOR DETACHABLE ARRAY

(71) Applicant: Novocure GmbH, Root (CH)

(72) Inventors: Yoram Wasserman, Haifa (IL); Stas Obuchovsky, Haifa (IL); Nataliya Kuplennik, Haifa (IL)

(73) Assignee: Novocure GmbH, Root (CH)

( * ) Notice: Subject to any disclaimer, the term of this patent is extended or adjusted under 35 U.S.C. 154(b) by 329 days.

(21) Appl. No.: 17/490,120

(22) Filed: Sep. 30, 2021

(65) Prior Publication Data

US 2022/0096819 A1    Mar. 31, 2022

Related U.S. Application Data

(60) Provisional application No. 63/216,749, filed on Jun. 30, 2021, provisional application No. 63/085,733, filed on Sep. 30, 2020.

(51) Int. Cl.
*A61N 1/04*      (2006.01)
*A61N 1/36*      (2006.01)
*A61N 1/40*      (2006.01)

(52) U.S. Cl.
CPC ....... *A61N 1/0476* (2013.01); *A61N 1/36002* (2017.08); *A61N 1/3603* (2017.08); *A61N 1/40* (2013.01)

(58) Field of Classification Search
CPC .................................................. A61N 1/36002
See application file for complete search history.

(56) References Cited

U.S. PATENT DOCUMENTS

| | | | | |
|---|---|---|---|---|
| 5,755,745 | A | * | 5/1998 | McGraw ............ A61N 1/36034 607/59 |
| 2010/0106204 | A1 | * | 4/2010 | Moffitt ...................... A61N 1/37 600/300 |
| 2018/0050200 | A1 | * | 2/2018 | Wasserman .............. A61N 1/40 |
| 2020/0155835 | A1 | * | 5/2020 | Wasserman .............. A61N 1/08 |

FOREIGN PATENT DOCUMENTS

| | | |
|---|---|---|
| KR | 100 892 663 B1 | 4/2009 |
| WO | WO 2009/068908 A2 | 6/2009 |
| WO | WO 2013/162816 A1 | 10/2013 |
| WO | WO 2017/220328 A1 | 12/2017 |

OTHER PUBLICATIONS

International Search Report and Written Opinion (PCT/IB2021/000664), dated Feb. 16, 2022, 12 pages.
International Search Report and Written Opinion (PCT/IB2021/000669), dated Feb. 22, 2022, 12 pages.

* cited by examiner

*Primary Examiner* — Michael W Kahelin
(74) *Attorney, Agent, or Firm* — DUNLAP CODDING, P.C.

(57) ABSTRACT

Apparatus and methods for imposing electric fields through a target region in a body of a patient are described. Generally, the apparatus includes at least one transducer array and a connector electrically connected to the at least one transducer array. The connector has at least one indicator electrical connector configured to provide feedback related to a status of the connector.

20 Claims, 25 Drawing Sheets

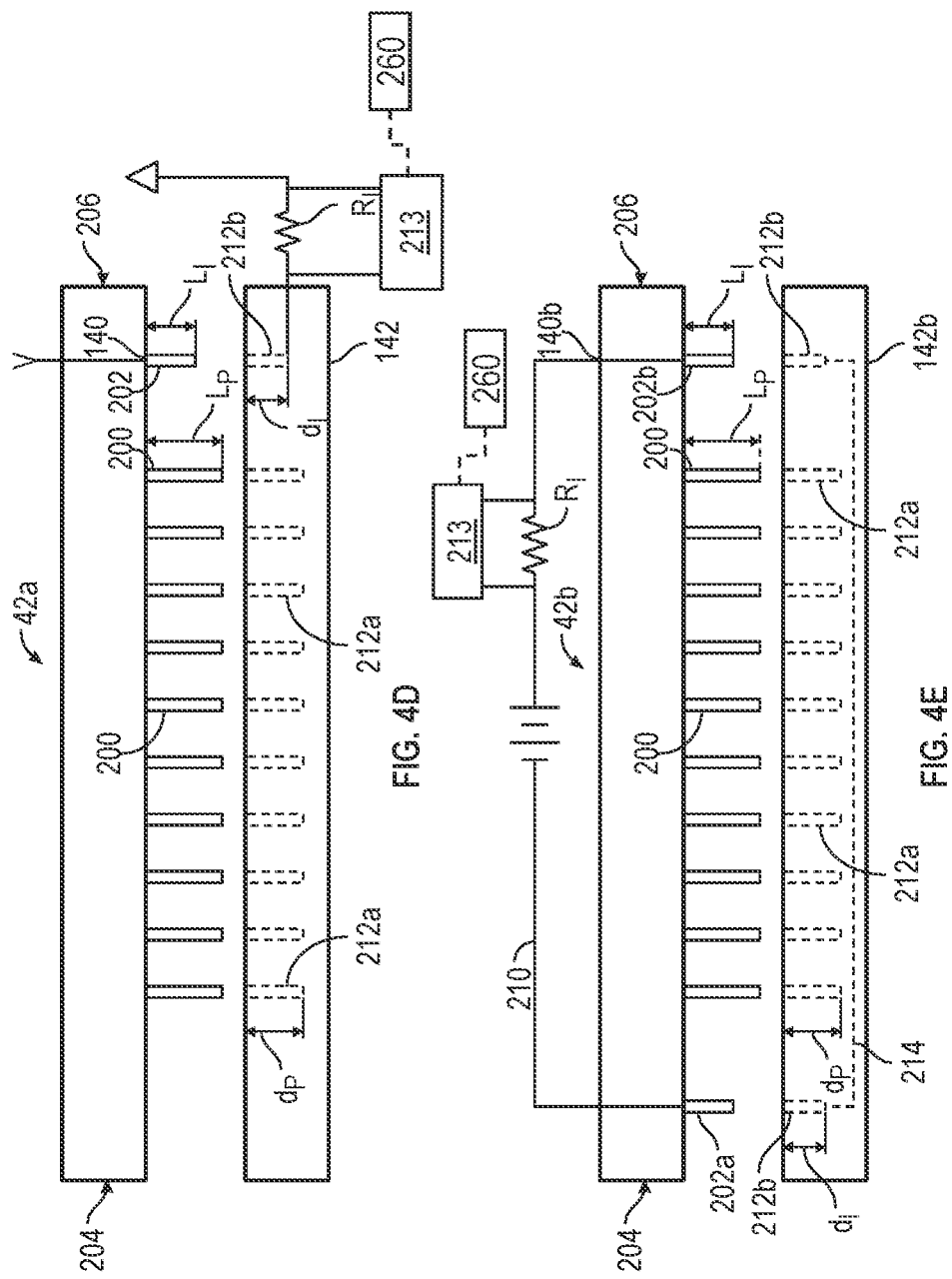

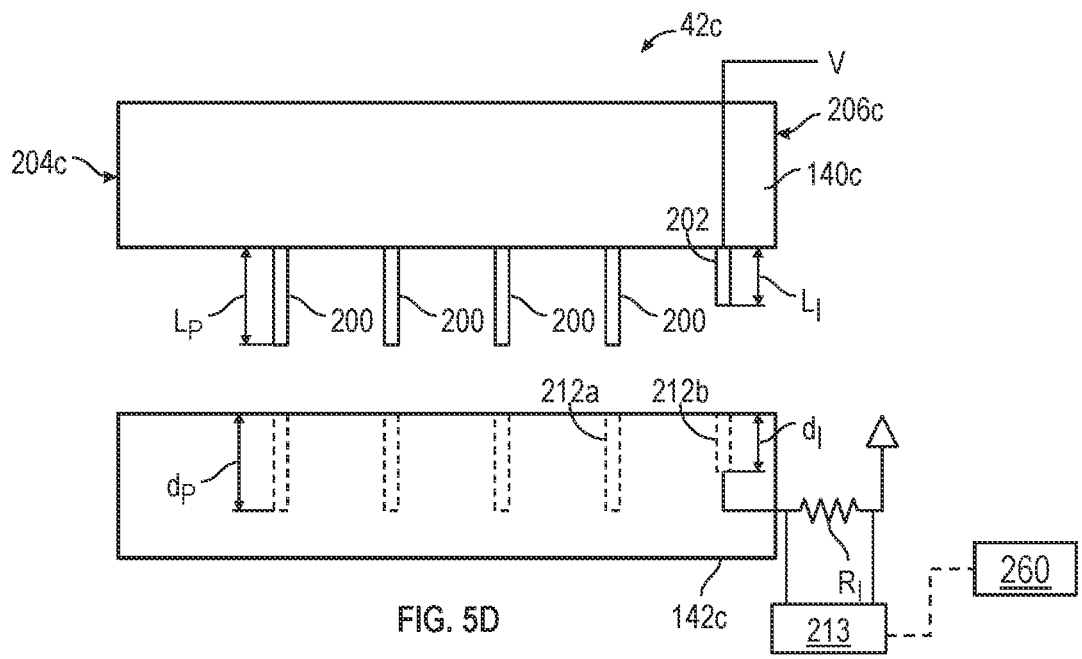
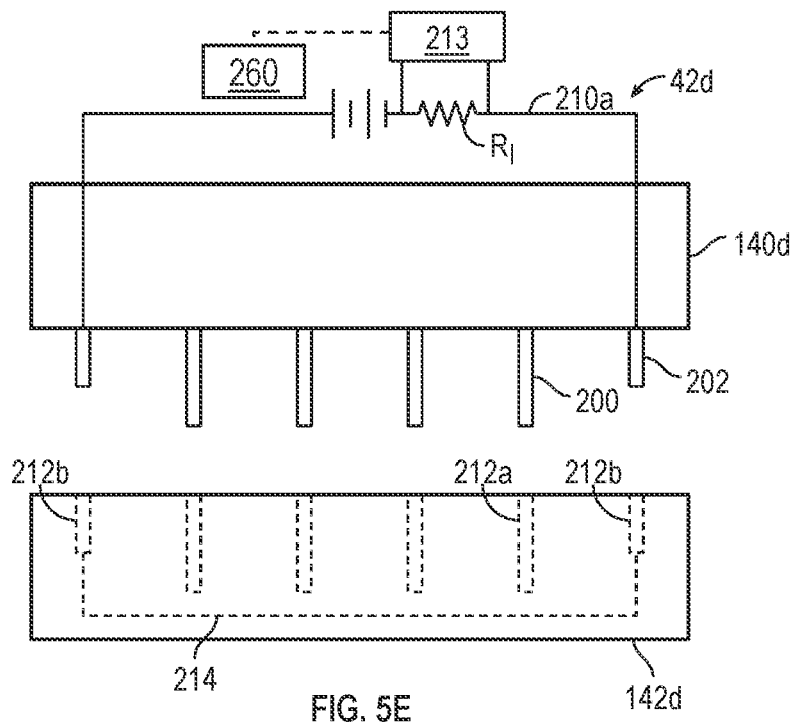
FIG. 5D
FIG. 5E

CONNECTOR FOR DETACHABLE ARRAY

CROSSREFERENCE TO RELATED APPLICATIONS/INCORPORATION BY REFERENCE STATEMENT

This application is a non-provisional application claiming benefit to U.S. Provisional Application No. 63/085,733, filed Sep. 30, 2020. This application also claims benefit to U.S. Provisional Application No. 63/216,749, filed Jun. 30, 2021. The entire contents of each of the above-referenced provisional applications is hereby expressly incorporated herein by reference.

BACKGROUND

TTFields therapy is a proven approach for treating tumors. For example, using the Optune® system for delivering tumor treating fields (i.e., TTFields), the TTFields are delivered to patients via four transducer arrays placed on the patient's skin in close proximity to a tumor. The transducer arrays are arranged in two pairs, and each transducer array is connected via a multi-wire cable to an electric field generator. The electric field generator (a) sends an AC current through one pair of arrays during a first period of time; then (b) sends an AC current through the other pair of arrays during a second period of time; then repeats steps (a) and (b) for the duration of the treatment.

SUMMARY OF THE INVENTION

A need exists for an apparatus and method for imposing electric fields through a target region in a body of a patient. Disclosed herein is an apparatus for imposing electric fields through a target region in a body of a patient, which apparatus comprises: at least one transducer array having a plurality of electrode elements configured for placement on the body of the patient, the electrode elements configured to provide TTFields; and a connector electrically connected to the at least one transducer array, wherein the connector has at least one associated monitoring circuit configured to provide feedback related to a status of the connector.

A method for monitoring an apparatus for imposing electric fields through a target region in a body of a patient is herein disclosed, the method comprising: electrically connecting a connector to at least one transducer array, wherein the at least one transducer array has a plurality of electrode elements configured for placement on the body of the patient, the electrode elements configured to provide TTFields; circulating current through at least one indicator pin integrated into a first portion of the connector, and an associated indicator socket connector integrated into a second portion of the connector; monitoring data from the circulating current; determining status of the connector based on the monitored data; and, providing a predetermined action based on the status of the connector.

A system is herein disclosed, the system comprising: a plurality of transducer arrays each having substrate supporting a plurality of electrode elements configured for placement on a body of a patient, the electrode elements configured to provide TTFields and at least one electrode element associated with a temperature sensor; each transducer array electrically connected to a first side of a connector, and each transducer array comprising a distal circuit electrically coupled to each of the plurality of electrode elements of the transducer array and operable to receive a temperature signal from each of the associated temperature sensors and operable to output a DATA signal and to receive a TTField Signal, the distal circuit being either supported by the substrate, or integrated into the first side of the connector, or both, or positioned in a circuit between the transducer array and the connector, the connector further comprising a plurality of pins or socket connectors in electrical communication with the transducer array; and, at least one monitoring circuit configured to provide feedback related to a status of the connector; a hub electrically coupled to each of the plurality of transducer arrays; and an electric field generator electrically coupled to the hub and operable to receive one or more DATA signal and output one or more TTField Signal.

An apparatus for imposing electric fields through a target region in a body of a patient is herein disclosed, the apparatus comprising: at least one transducer array having a plurality of electrode elements configured for placement on the body of the patient and at least one temperature sensor, the electrode elements configured to provide TTFields; a distal circuit electrically coupled to the at least one transducer array and operable to receive a temperature signal from the at least one temperature sensor; and a connector electrically connected to the distal circuit, the distal circuit positioned in a circuit between the transducer array and the connector.

A system is herein disclosed, the system comprising: a plurality of transducer arrays each having substrate supporting a plurality of electrode elements configured for placement on the body of a patient, the electrode elements configured to provide TTFields and at least one electrode element associated with a temperature sensor; each transducer array electrically connected to a first side of a connector, and each transducer array comprising a distal circuit electrically coupled to each of the plurality of electrode elements of the transducer array and operable to receive a temperature signal from each of the associated temperature sensors and operable to output a DATA signal and to receive a TTField Signal, the distal circuit being either supported by the substrate, or integrated into the first side of the connector, or both, or positioned in a circuit between the transducer array and the connector; a hub electrically coupled to each of the plurality of transducer arrays; and an electric field generator electrically coupled to the hub and operable to receive one or more DATA signal and output one or more TTField Signal.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings:

FIGS. 4A-4F illustrate exemplary embodiments of connectors for use in the system illustrated in FIG. 1 in accordance with the present disclosure. The exemplary connectors may be positioned between one or more transducer arrays and one or more distal circuits.

FIGS. 5A-5G illustrates exemplary embodiments of connectors for use in the system illustrated in FIG. 1 in accordance with the present disclosure. The exemplary connectors may be positioned between one or more distal circuits and one or more hubs.

DETAILED DESCRIPTION

Figure 1:
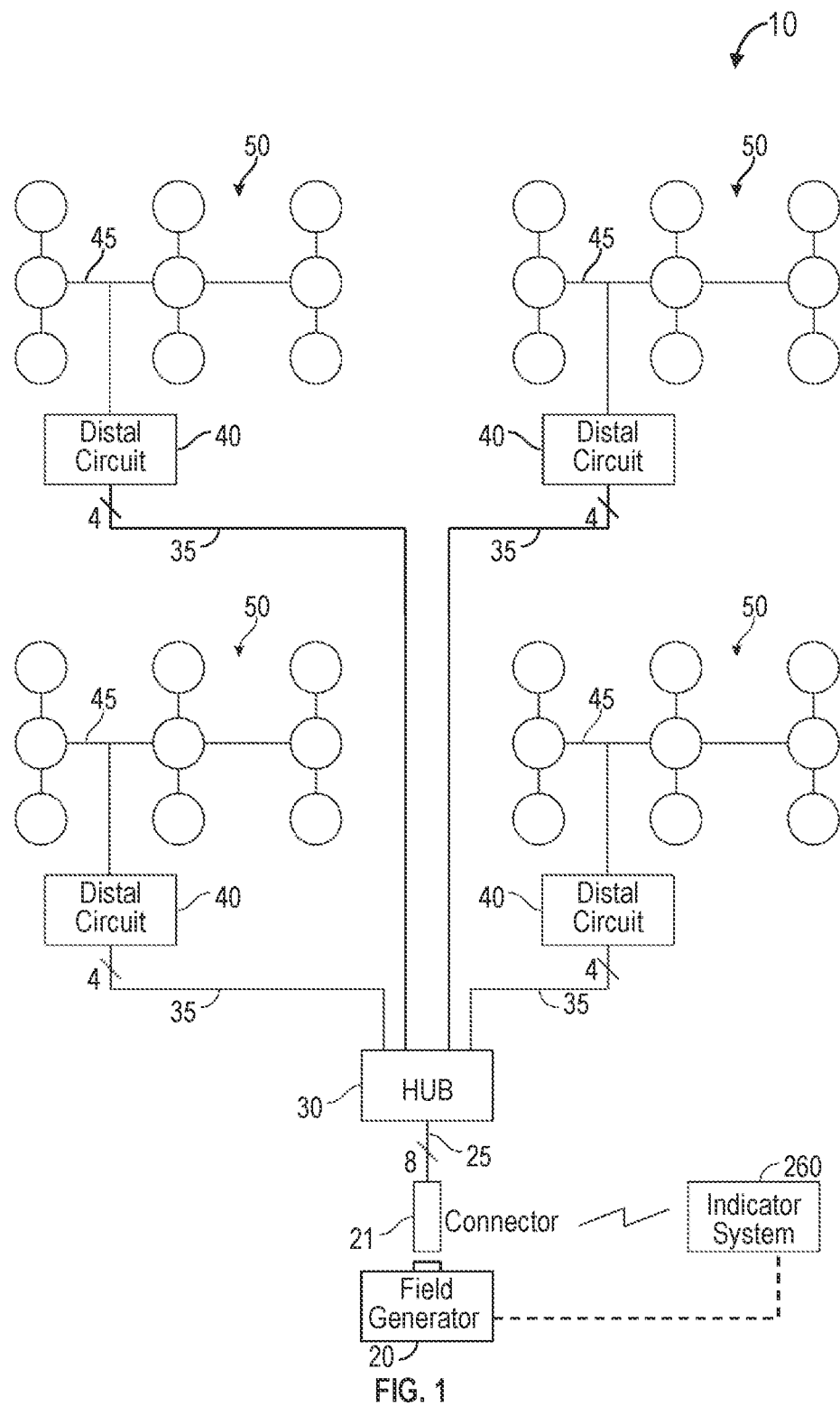
FIG. 1 is a block diagram of an exemplary system for measuring the temperature of transducer arrays applying TTFields to a body of a patient in accordance with the present disclosure.

The TTFields are generally delivered to patients via four transducer arrays placed on the patient's skin conventionally as two orthogonal pairs in locations chosen to best target the tumor. Each transducer array is configured as a set of coupled electrode elements (for example, about 2 cm in diameter) that are interconnected via flex wires. Commonly, each electrode element includes a ceramic disk that is sandwiched between a layer of an electrically conductive medical gel and an adhesive tape. When placing the arrays on the patient, the medical gel adheres to the contours of the patient's skin and ensures good electrical contact of the device with the body. The adhesive tape holds the entire array in place on the patient as the patient goes about their daily activities.

The amplitude of the alternating current that is delivered via the transducer arrays is controlled so that skin temperature (as measured on the skin below the transducer arrays) does not exceed a safety threshold of 41 degrees Celsius. The temperature measurements on the patient's skin are obtained using thermistors placed beneath some of the disks of the transducer arrays. In the existing Optune® system, each array includes 8 thermistors, with one thermistor positioned beneath a respective disk in the array.

The thermistors in each of the four arrays are connected via long wires to an electronic device called the "cable box" where the temperature from all 32 thermistors (i.e., four (4) arrays×eight (8) thermistors per array) is measured and analog-to-digital converted into digital values for each thermistor. These measurements are then transmitted from the cable box to the electric field generator via an additional two wires that facilitate two-way digital serial communications between the cable box and the electric field generator. The controller in the electric field generator uses the temperature measurements to control the current to be delivered via each pair of arrays in order to maintain temperatures below 41 degrees Celsius on the patient's skin. The current itself is delivered to each array via an additional wire (i.e., one wire for each array) that runs from the electric field generator through the cable box to the array.

In the existing Optune® system there are four long 10-wire cables (each of which runs between a respective array and the cable box) and one 8-wire spiral cord that runs between the electric field generator and the cable box. Each of the 10-wire cables has 8 wires for carrying signals from the 8 thermistors, 1 wire for the common ground of all 8 thermistors, plus 1 wire for providing the TTFields signal to the array. The 8-wire spiral cord has 1 wire for power to the cable box (Vcc), 1 wire for ground to the cable box, 2 wires for data communication (to send the temperature readings to the field generator), plus 4 wires for TTFields signal (i.e., one for each of the four arrays).

Attaching temperature sensors and transducer arrays to a patient is cumbersome with the number of wires. As such, a connector may be used to provide a detachable transducer array. Such connector may also allow for reuse of wiring within the device. Generally, the connector may be formed of waterproof materials. However, movement of a patient may inadvertently loosen and/or detach the connecter. As such, there is a need for detection and/or indication of status of conditions at the connector to provide a safe and/or effective treatment for a patient.

Therefore, a need exists for an apparatus for imposing electric fields through a target region in a body of a patient while minimizing cumbersome wiring associated with the apparatus. The apparatus comprises at least one transducer array having a plurality of electrode elements configured for placement on the body of the patient and at least one temperature sensor. The electrode elements are configured to provide TTFields. A distal circuit is electrically coupled to the at least one transducer array and operable to receive a temperature signal from the at least one temperature sensor. In some embodiments, a connector is electrically connected to the distal circuit and the distal circuit positioned in a circuit between the transducer array and the connector. Further, the apparatus may include at least one indicator electrical connector configured to provide feedback related to a status of the connector.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular.

All of the compositions, assemblies, systems, kits, and/or methods disclosed herein can be made and executed without undue experimentation in light of the present disclosure. While the compositions, assemblies, systems, kits, and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect.

Headings are provided for convenience only and are not to be construed to limit the invention in any manner. Embodiments illustrated under any heading or in any portion of the disclosure may be combined with embodiments illustrated under the same or any other heading or other portion of the disclosure. Any combination of the elements described herein in all possible variations thereof is encompassed by the invention unless otherwise indicated herein or otherwise clearly contradicted by context.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, or greater numbers of compounds. The term "plurality" refers to "two or more."

The use of the term "at least one" will be understood to include one as well as any quantity more than one. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "patient" as used herein encompasses any mammals including human and veterinary subjects. "Mammal" for purposes of treatment refers to any animal classified as a mammal, including (but not limited to) humans, domestic and farm animals, nonhuman primates, and any other animal that has mammary tissue. In some embodiments, the term "patient" may apply to a simulation mannequin for use in teaching, for example.

The treatments of the present disclosure may be used as part of a combination therapy, concurrent therapy, or adjunct therapy. As used herein, such terms are used interchangeably and will be understood to mean that the patient in need of treatment may be treated or given another drug for the condition/disease/infection in conjunction with the treatments of the present disclosure. This concurrent therapy can be sequential therapy, where the patient is treated first with one treatment protocol/pharmaceutical composition and then the other treatment protocol/pharmaceutical composition, or the two treatment protocols/pharmaceutical compositions are given simultaneously.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

The term "TTField", as used herein, means tumor treating field.

Figure 2:
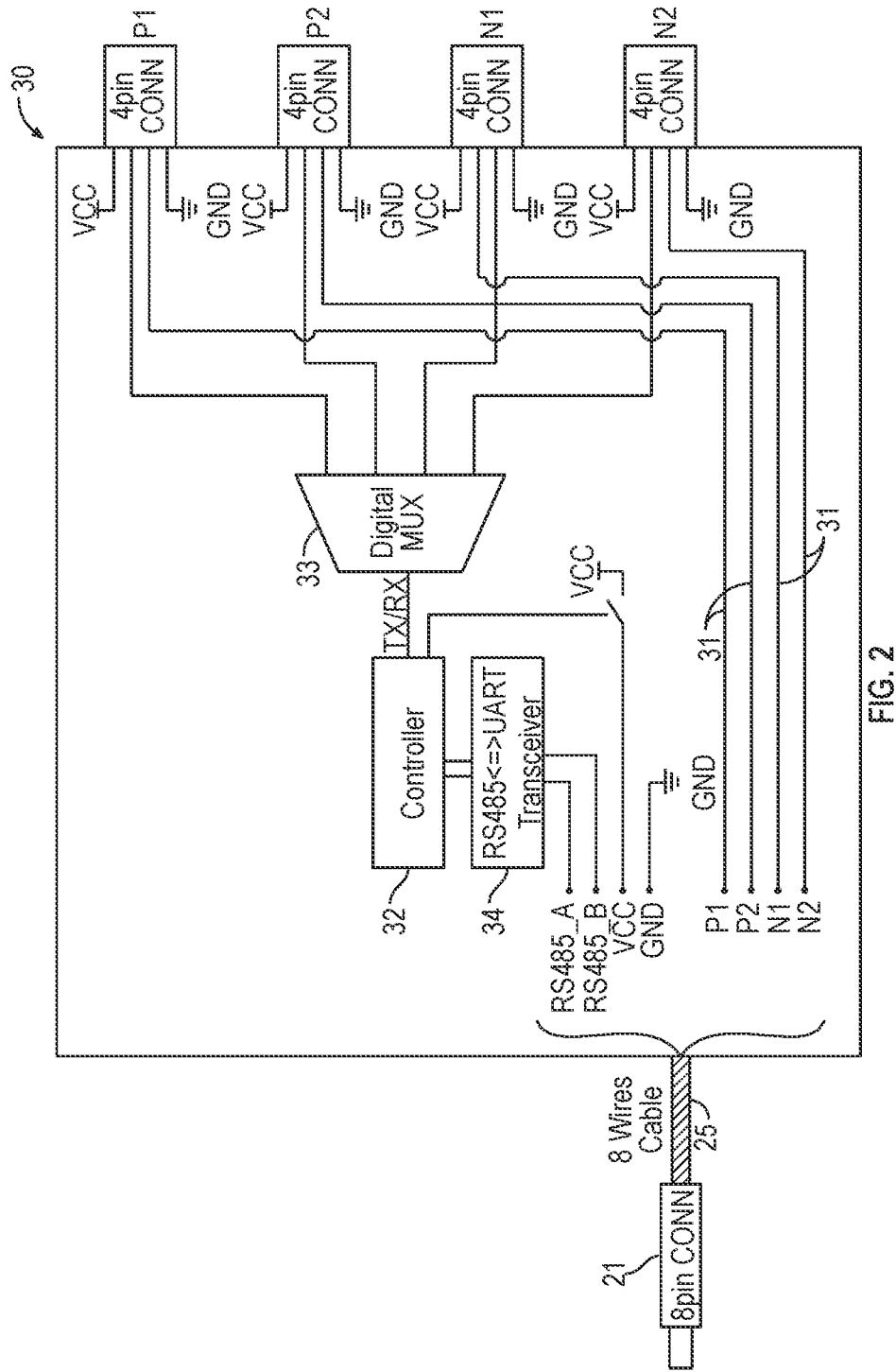
FIG. 2 is a schematic diagram of an exemplary hub for use in the system illustrated in FIG. 1 in accordance with the present disclosure.
Figure 3:
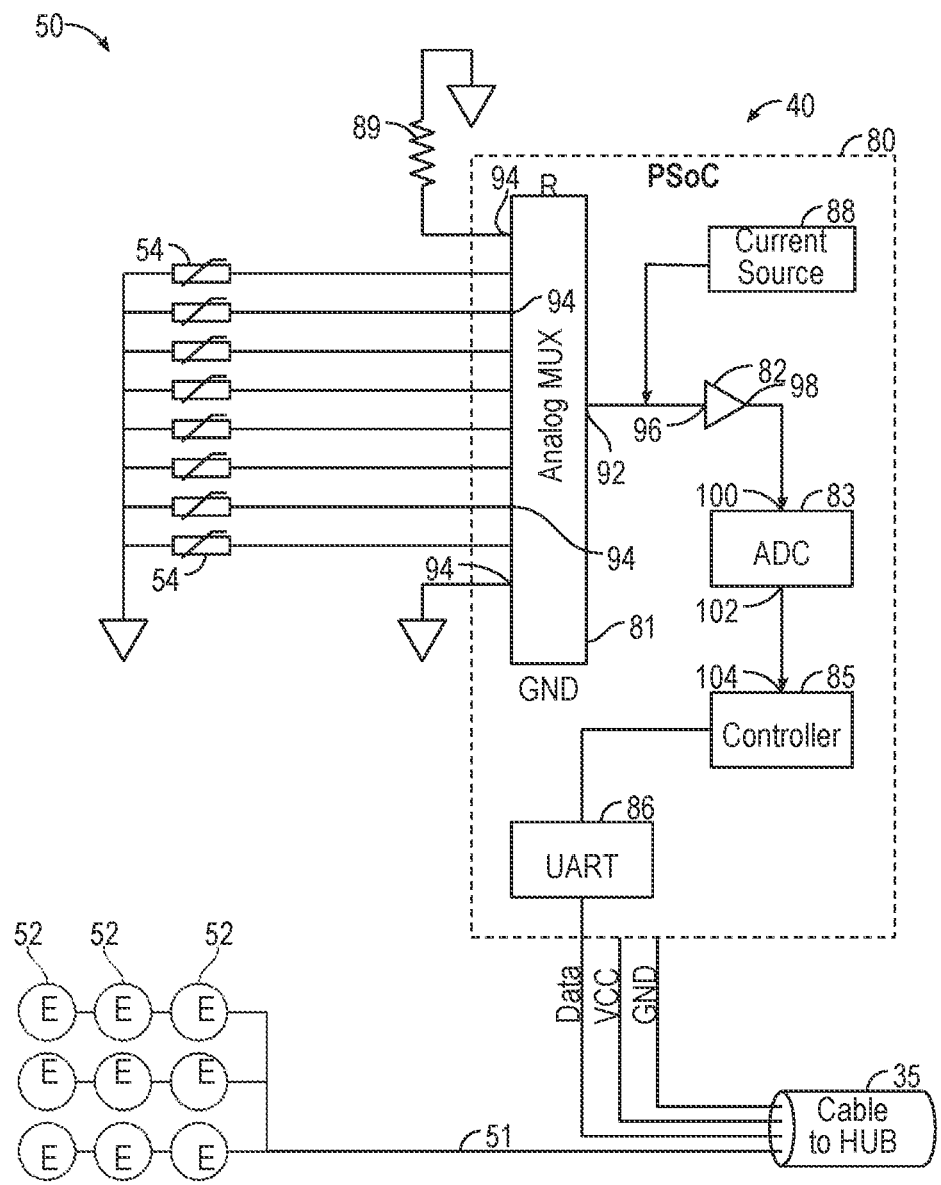
FIG. 3 is a schematic diagram of an exemplary distal circuit for use in the system illustrated in FIG. 1 in accordance with the present disclosure.

Referring now to the drawings, and in particular FIGS. 1-3, shown therein are block diagrams of an exemplary embodiment of a system 10 having one or more distal circuits 40 positioned in close proximity to one or more transducer arrays 50 to obtain one or more temperature readings from one or more temperature sensors 54 (see FIG. 3). Each of the transducer arrays 50 includes one or more electrode elements 52 (see FIG. 3). The one or more temperature sensors 54 are positioned to detect the temperature at the electrode elements 52. In some embodiments, the temperature sensors 54 may be thermistors, thermocouples, RTDs, integrated circuit temperature sensors such as the Analog Devices AD590 and the Texas Instruments LM135, and/or combinations thereof.

Alternative constructions for the transducer arrays may be used, including, for example, transducer arrays that use ceramic elements that are disc-shaped, transducer arrays that use ceramic elements that are not disc-shaped, and transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array would be implemented using a region of a conductive material that is configured for placement against a person's body, with no insulating dielectric layer disposed between the conductive elements and the body. Examples of the conductive material include a conductive film, a conductive fabric, and a conductive foam. Other alternative constructions for implementing the transducer arrays may also be used, as long as they are (a) capable of delivering TTFields to the person's body and (b) utilize the improved connector designs described herein positioned in the locations specified herein. Optionally, a layer of hydrogel may be disposed between the transducer arrays and the person's body in any of the embodiments described herein.

In the event that a transducer array may be too large, or of an unsuitable shape to conveniently conform to the desired location of the body (for example, an array to be positioned on the side of the head where the ears partially block the desired location of the array), the array may be cut to a more convenient size and/or shape. Where the cutting is desired to occur through the printed circuit board of the array, exposed wires may be sealed off to prevent direct contact with the skin. Sealing off exposed wiring may be achieved, for example, by enclosing the printed circuit board with a tape known as bubble glue tape. The latter comprises a plurality of bubbles containing a liquid component A, and a plurality of bubbles containing a liquid component B, where components A and B are components of a reactive 2-pack epoxy. Preferably, the two types of bubbles are homogeneously distributed on the tape and in close contact such that cutting through the tape (and through the printed circuit board wiring) causes adjacent bubbles to be cut open effecting a mixing of the components A and B with subsequent reaction to form a solid film over the exposed wiring. A rapid-set 2-pack epoxy system, having suitable viscosity, can be used to flow just enough to mix, react and seal the cut edge of the printed circuit board.

Each distal circuit 40 interfaces with the one or more temperature sensors 54 that are incorporated into the respective transducer array to obtain temperature readings from each of the one or more temperature sensor 54. The distal circuit 40 then may convert (e.g., analog to digital) the temperature readings, forward the temperature reading and/or send the temperature readings to a hub 30 (See FIG. 1). The hub 30 may then forward the temperature reading and/or send the temperature readings to an electric field generator 20 (e.g., via a serial communication link). In some embodiments, the electric field generator 20 may determine, based on the temperature readings, adjustment of the current to the transducer arrays 50.

In some embodiments, short conductors (e.g., ten short conductors) may extend distally in the wiring 45 beyond the distal circuit 40 into the transducer array 50. The short conductors may include, for example, one conductor for each of one or more temperature sensors 54, one conductor for the one or more temperature sensors' common ground, and one conductor for the TTFields signal (i.e., the AC current for the electrode elements). In some embodiments, the distal circuit 40 may be implemented using a single-chip microcontroller or Programmable System on Chip (PSoC) with a built in analog front end and multiplexer. Suitable part numbers for this purpose include the CY8C4124LQI-443, manufactured by the Cypress Semiconductor Corp., having a principal place of business in San Jose, California. As one skilled in the art will appreciate, some embodiments may include one or more microcontrollers having built-in and/or discrete analog front ends and/or multiplexers. For example, the analog front end and multiplexer may obtain temperature readings from the one or more temperature sensors 54. Those temperature readings may then be digitized and/or transmitted to the hub 30, (e.g., via serial data link). In some embodiments, each distal circuit 40 may also include one or more pass-through conductors 51 (see FIG. 3). The one or more pass-through conductors 51 may be configured to route one or more TTFields signal that originated in the electric field generator 20 to the transducer array 50.

Referring to FIGS. 1 and 3, each distal circuit 40 may be connected to the hub 30 via one or more cable 35. Conductors 51 in each cable 35 may run between the distal circuit 40 and the hub 30. For example, in FIG. 3, four conductors 51 run between each distal circuit 40 and the hub 30, including, one conductor 51 for power (Vcc), one conductor 51 for grounding (GND), one conductor for serial data communication (DATA), and one for the TTField Signal.

FIG. 2 is a schematic diagram of a circuit for an exemplary hub 30 for use in the system 10 illustrated in FIG. 1. Generally, the hub 30 may receive one or more temperature readings from each of the distal circuits 40 and sends the one or more temperature readings to the electric field generator 20. Any of a wide variety of architectures may be used to receive and send the one or more temperature readings. For example, in the illustrated embodiment, a controller 32 sends a signal to a digital multiplexer 33 that commands the digital multiplexer 33 to select one of the distal circuits 40 such that the hub 30 may receive digital data from the distal circuit 40 (i.e., the first distal circuit). The controller 32 receives the one or more temperature readings from the selected input of the first distal circuit 40 and transmits the one or more temperature readings to the electric field generator 20 via the transceiver 34. The controller 32 may then update the control signal to the digital multiplexer 33 such that the digital multiplexer 33 selects another distal circuit 40 (i.e., the second distal circuit 40). The controller 32 then receives one or more temperature readings from the input of the second distal circuit 40 and transmits one or more temperature readings to the electric field generator 20. Corresponding sequences may then be performed to obtain suitable temperature readings (e.g., eight temperature readings) from each of the distal circuits 40. In some embodiments, the entire sequence of obtaining each of the one or more temperature readings from each of the distal circuits 40 or a portion of the sequence may be repeated periodically (e.g., every 1 second, 10 seconds, or 30 seconds) to update the one or more temperature readings that are provided to the electric field generator 20.

In some embodiments, the controller 32, the digital multiplexer 33, and/or the transceiver 34 may be integrated together into a single chip. In some embodiments, the controller 32 and the digital multiplexer 33 may be integrated together into a single chip, and a separate transceiver 34 is used. For example, the controller 32 and the digital multiplexer 33 may be implemented using a Cypress CY8C4244LQI-443, manufactured by Cypress Semiconductor Corp., having a principal place of business in San Jose, California, and the transceiver 34 may be implemented using a Linear Technology LTC2856CMS8-2 #PBF, manufactured by Linear Technology Corp., having a principal place of business in Milpitas, California.

The hub 30 may communicate with the electric field generator 20 using any conventional communication technique (e.g., RS485). In some embodiments, the hub 30 may include one or more pass-through conductors 31 configured to pass one or more TTField signals directly from the electric field generator 20 to each of the transducer arrays 50. In some embodiments, the hub 30 may communicate with the electric field generator 20 via an 8-conductor spiral cable 25. For example, the hub 30 may communicate with the electric field generator 20 via an 8-conductor spiral cable 25 wherein four wires may provide for TTFields signals to be received by each transducer array 50, one wire may provide for ground (GND), one wire may provide for voltage (Vcc) to the distal circuits 40, and two wires may provide for communication (RS485A and RS485B). It should be noted that use of the 8-conductor spiral cable 25 is configured to be backwards compatible with prior versions of TTField delivery systems within the art as one skilled in the art will appreciate.

Communication wires may be configured to implement data communications between the hub 30 and the electric field generator 20 (see FIG. 1) (i.e., for the temperature data). In some embodiments, one wire may be configured to implement communication in each direction. In some embodiments, wire count between the hub 30 and the electric field generator 20 can be reduced by replacing multiple data communication wires with a single data wire that implements two-way communication (using a conventional single wire communication protocol).

FIG. 3 is a schematic diagram of an exemplary circuit for interfacing the hub 30 with the one or more transducer array 50. Each transducer array 50 may include one or more electrode elements 52 and one or more temperature sensors 54 positioned to sense temperatures of the one or more electrode elements 52. In some embodiments, one or more temperature sensors 54 may be thermistors. For example, the one or more temperature sensors 54 may include, but are not limited to, thermistors, thermocouples, RTDs, integrated circuit temperature sensors such as the Analog Devices AD590 and the Texas Instruments LM135, and/or combinations thereof. It is contemplated that any temperature sensor 54 known within the art may be used if configured to provide an accurate and/or precise temperature reading in accordance with the present disclosure.

A multiplexer 81 may include an output 92 and one or more selectable inputs 94. Each of one or more selectable inputs 94 may be connected to a respective one of the temperature sensors 54. At least one terminal of each temperature sensor 54 may be a common ground. In some embodiments, the output 92 of the multiplexer 81 may be provided to an input 96 of an amplifier 82, (e.g., amplifier having a high input impedance such as an op amp configured as a voltage follower). Output 98 of the amplifier 82 may be provided to an input 100 of an analog to digital converter 83. Output 102 of the analog to digital converter is provided to input 104 of a controller 85.

In some embodiments, the controller 85 may be configured to orchestrate operation of one or more of the components within the dashed line 80. The controller 85 may be configured to send one or more commands to the multiplexer 81 to select one of the temperature sensors 54, in order to obtain a temperature reading from that temperature sensor 54.

In some embodiments, temperature readings may be obtained by routing a known current through the temperature sensor 54 (e.g., thermistor) and measuring the voltage that appears across the temperature sensor 54. For example, a programmable current source 88 may be configured to generate a known current (e.g., 150 µA). The multiplexer 81 may be bidirectional such that the known current may be routed to the temperature sensor 54 selected by the multiplexer 81.

In some embodiments, temperature readings from the one or more temperature sensors 54 may be obtained using the following method. The controller 85 sends one or more commands to the multiplexer 81 to select the first temperature sensor 54, and configures the current source 88 to generate a known current. The known current from the current source 88 is configured to flow through the multiplexer 81 into the first temperature sensor 54 resulting in a voltage appearing across that temperature sensor 54 and at the output 92 of the multiplexer 81. The amplifier 82 provides this voltage to the input 100 of the analog to digital converter 83. The controller 85 instructs the analog to digital converter 83 to digitize this voltage. The controller 85 obtains this reading from the analog to digital converter 83 and temporarily stores the digitized reading (which corresponds to the first temperature sensor 54) in a buffer. This procedure may be repeated, sequentially, for each of the temperature sensors 54 until digitized readings from each requested temperature sensor 54 is within the buffer.

In some embodiments, a conventional voltage divider approach for interfacing with the one or more temperature sensors 54 may be used. In some embodiments, additional readings may be obtained and used for self-calibration to increase the accuracy and/or precision of the temperature readings obtained from the one or more temperature sensors 54. For example, in FIG. 3, at least one input $94_{GND}$ of the multiplexer 81 is connected to ground, and at least one input 94R of the multiplexer 81 is connected to a precision resistor 89. In some embodiments, the precision resistor 89 is a 10 kOhm, 0.1% tolerance resistor. Readings from the precision resistor 89 may be obtained using the same procedure described above for obtaining a reading from the one or more temperature sensors 54. Obtaining readings from the grounded input $94_{GND}$ of the multiplexer 81 may also be similar, except that the current source 88 may be deactivated when the grounded input $94_{GND}$ is selected. The controller 85 may temporarily store the digitized readings from the precision resistor 89 and the grounded input $94_{GND}$ in a buffer (e.g., total of 10 readings are stored in the buffer) and/or any memory configured to store data. These additional readings may ultimately be used to calibrate the readings that were obtained from the one or more temperature sensors 54. In some embodiments, such calibration may be implemented via the controller 85. In some embodiments, calibration may occur prior to transmission of the digital data that corresponds to the temperature readings. In some embodiments, calibration may be implemented in a downstream processor (e.g., the controller 32 in the hub 30) such that the digital data corresponding to the precision resistor 89 (and optionally the grounded input $94_{GND}$) may be transmitted to a downstream processor, in addition to, any uncalibrated temperature readings obtained from the one or more temperature sensor 54.

In some embodiments, calibration using the precision resistor 89 may compare the actual voltage measured across the precision resistor 89 with an expected voltage based on Ohm's law, the known value of the precision resistor 89, and the expected value of the current being produced by the current source 88. Deviations between the actual measured voltage and the expected voltage may be used to determine subsequent measurements (e.g., use as a multiplier) from the one or more temperature sensors 54.

In some embodiments, the controller 85 in the distal circuit 40 may be configured to communicate with the hub 30 via UART 86, and transmit the temperature readings obtained from the one or more temperature sensors 54 to the hub 30. In some embodiments, the controller 85 may be programmed to operate autonomously and configured to automatically collect temperature readings from each of the one or more temperature sensors 54, storing the result in a buffer as described above, and subsequently transmitting contents of the buffer (i.e., readings for each of the temperature sensors 54, and optionally the additional readings described herein) to the hub 30.

In some embodiments, the controller 85 may be programmed to operate as a slave controller to a master controller located in the hub 30. For example, the controller 85 may begin in a quiescent state, wherein the controller 85 solely monitors incoming commands from the master controller that arrive via the UART 86. Examples of commands that can arrive from the master controller may include, but are not limited to, "collect samples" command, "send data" command, and/or the like. When the controller 85 recognizes that a "collect samples" command has arrived, the controller 85 may be configured to initiate the method described herein to obtain one or more temperature readings from the one or more temperature sensors 54, and store results in the buffer and/or any memory configured to store data. In another example, the controller 85 may recognize a "send data" command, and execute a method to transmit previously collected temperature readings from the buffer and/or memory to the hub 30 via the UART 86.

In some embodiments, temperature measurements may be synchronized. For example, the master controller in the hub 30 may send a "collect samples" command to one or more controllers 85 either simultaneously or in rapid succession, such that the temperature readings obtained from each of the transducer arrays 50 may be obtained at or near the same time. In some embodiments, the temperature readings may be collected by the hub 30 in one or more batches of each controller 85.

Most systems that use TTFields to treat tumors switch the direction of the field that is being applied to the tumor periodically (e.g., every second). To minimize noise in the temperature measurements, a small time gap during which the field is not applied in either direction may be introduced, and the temperature measurements can be made during the time gap. In some embodiments, the master controller (e.g., the controller 32) located in the hub 30 may synchronize timing of the "collect samples" command to all controllers 85 such that each of the distal circuits 40 may obtain temperature readings during the time gap. The temperature readings simultaneously obtained from each transducer arrays 50 may minimize duration of the time gap. For example, if the system 10 requires 100 μs to obtain a single measurement, taking thirty-two measurements in sequence (i.e., four distal circuits×eight temperature sensors 54 at each distal circuit 40) may take 3.2 ms. In contrast, if each of four distal circuits 40 operates in parallel, each distal circuit 40 can complete its job in 800 μs, such that 32 samples can be obtained in 800 μs. It should be noted that the "send data" command may not be sensitive to noise such that the "send data" command can be executed while the fields remain on, and as such, is not time-critical.

In some embodiments, some or all of the following components may be implemented by a single integrated circuit: multiplexer 81, amplifier 82, analog to digital converter 83, controller 85, UART 86, and current source 88. One example of a single integrated circuit that includes all of these functional blocks is the Cypress CY8C4124LQI-443T programmable system on chip (PSoC), manufactured by Cypress Semiconductor Corp., having a principal place of business in San Jose, CA.

In some embodiments, wires that provide power and ground to the distal circuit 40 can be eliminated by diverting some of the energy from the TTFields signal (which is delivered via pass-through conductors) using a coil, storing that energy in a capacitor adjacent to the distal circuit 40, and powering the distal circuit 40 using the stored energy. In some embodiments, a one-wire communication protocol may transmit the temperature data over the TTFields signal wire. In such a configuration, the data communication signals and power (Vcc) for the distal circuit 40 may be removed from the cable that runs to the transducer array 50. If all of these wire reduction techniques are implemented, only two wires may be needed between the hub 30 and each transducer array 50 (i.e., 1 for the TTField signal and 1 for ground). As such, the total number of wires from the four transducer arrays 50 to the electric field generator 20 may be reduced (e.g., to 5 total wires with 1 for a common ground and a total of 4 for the TTField signals).

The process of monitoring the temperature at the electrodes allows for operation of the TTFields treatment while staying below the temperature safety threshold, but introduces cumbersome apparatus and wiring. The use of a connector adds the convenience of detaching the transducer arrays. However, the electric field generator should be powered down prior to disconnecting the connector, and accidental disconnection of the connector is to be avoided.

Referring to FIGS. 4A-4F, one or more connectors 42 may be included between the hub 30 and one or more of the transducer arrays 50. Connectors 42 may be configured such that a patient and/or caregiver may be able to attach the transducer arrays 50 to the patient's skin without being hindered by the presence of cables. In some embodiments, one or more connectors 42 may be waterproof to prevent moisture (e.g., perspiration, showers, etc.) from interfering with the electric circuitry.

In some embodiments, the one or more connectors 42 may be positioned between the transducer array 50 and the hub 30. In some embodiments, the connector 42 may be positioned between the transducer array 50 and the distal circuit 40 as shown by connector 42*a* in FIGS. 4A-4F.

Generally, the one or more connectors 42 may be electrically connected to the at least one transducer array 50. The one or more connectors 42 may include a plurality of electrical connectors 200 in electrical communication with the one or more transducer array 50. Additionally, the one or more connectors 42 may include at least one indicator electrical connector 202 electrically isolated from the one or more transducer array 50 in order to provide a warning that the connector is disconnecting and the electric field generator should be powered down. The at least one indicator electrical connector 202 may be configured to provide feedback related to status of the connector 42. In some embodiments, the at least one indicator electrical connector 202 includes two indicator electrical connectors with the connector 42 having a conductive line 214 electrically connecting the two indicator electrical connectors 202. The at least one indicator electrical connector 202 may have a gender, such as male or female. By way of example, the indicator electrical connector 202 will be described hereinafter as an indicator pin 202, although other constructs may be used, such as, for example, a pinch clip which may optionally be deliberately triggered by the patient to release the connector (and simultaneously send a command to the electric field generator to power down). In some embodiments, the indicator pins 202 have a first length less than a second length of at least one of the plurality of electrical connectors 200. For clarity and conciseness, the description set forth herein refers to the electrical connectors 200 and indicator electrical connectors 202 as "pins" or "sockets"; however, one skilled in the art will appreciate that the electrical connectors 200 and indicator electrical connectors 202 do not necessarily have "pins" or "sockets", and may be any device configured to have electrical communication with the one or more transducer arrays 50 as set forth in the description. For example, a USB-type connector may be adapted by presenting one or more conductive trace within the connector that is shorter compared to others therein, and may be adapted to provide indication of an incomplete connection. Preferably, the mechanism allows for quick release if desired (deliberate), and also for detection of (accidental) release or disconnect, preferably prior to full disconnect. In some embodiments, the connector includes a quick release mechanism that is activated by a sensor that detects the patient depressing a button on the apparatus to disconnect the connector.

Figure 4A:
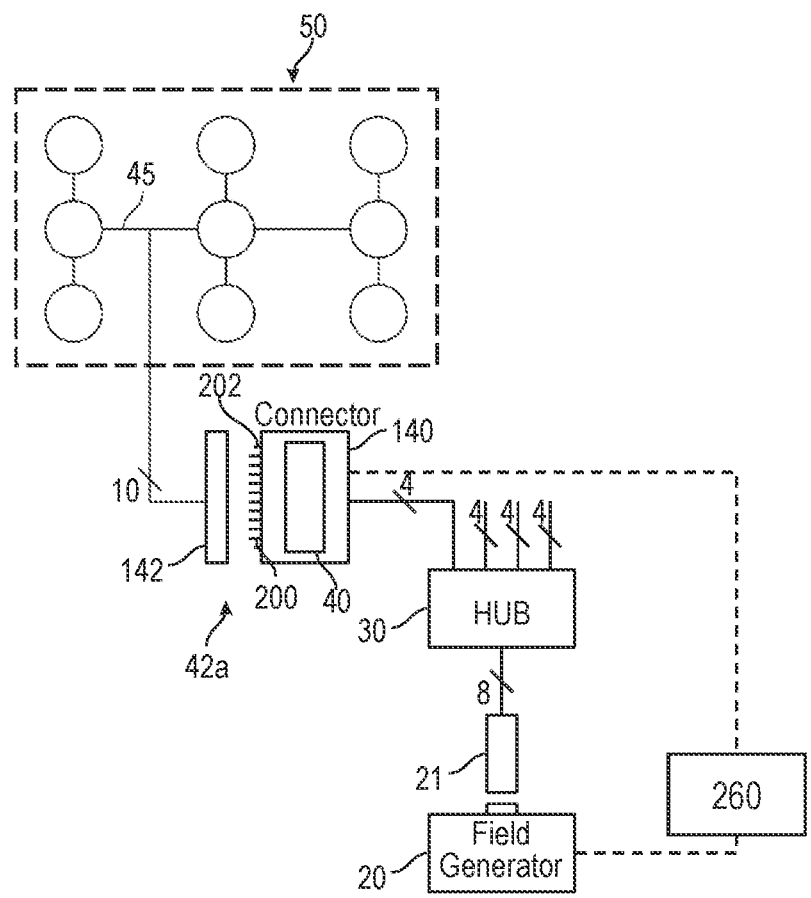
Figure 4B:
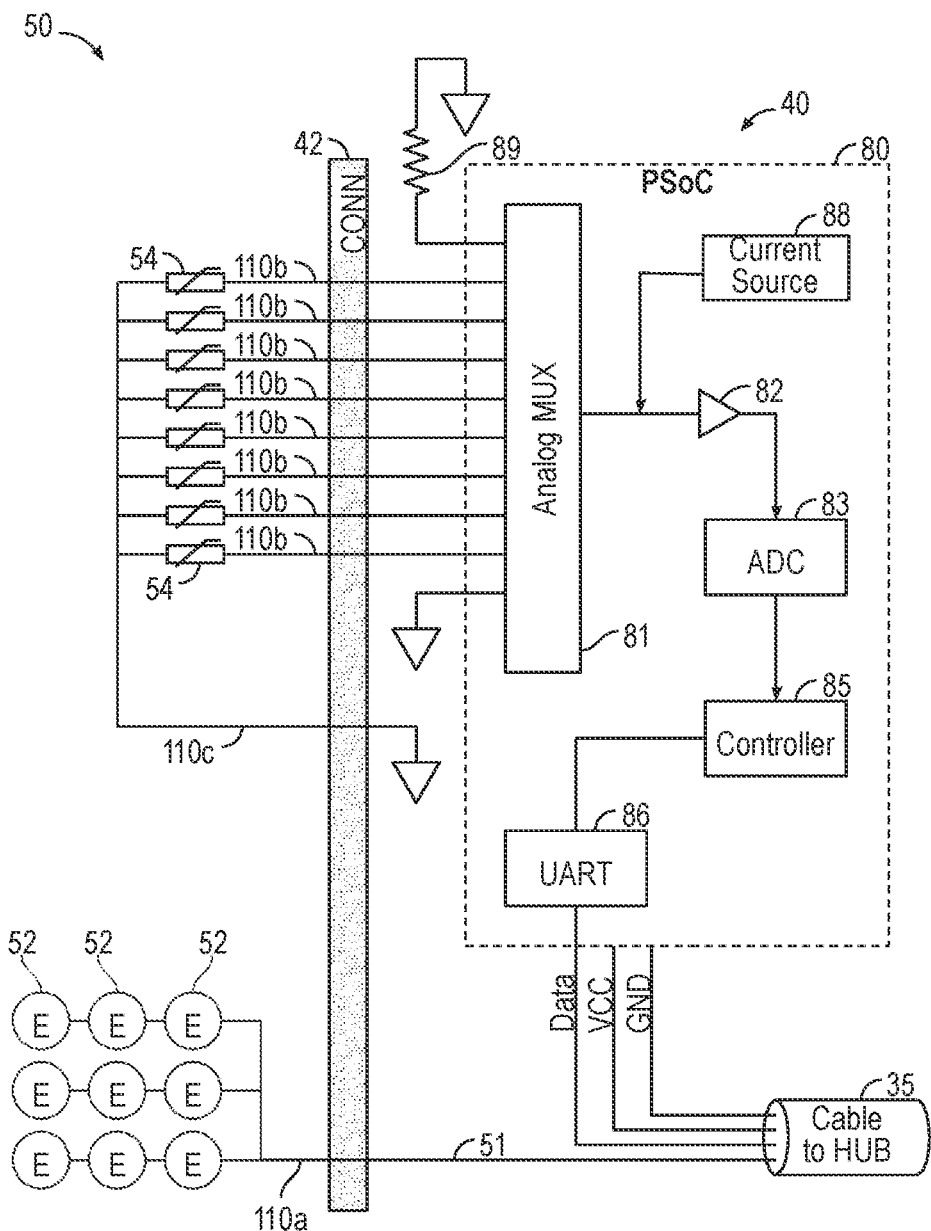
Figure 4C:
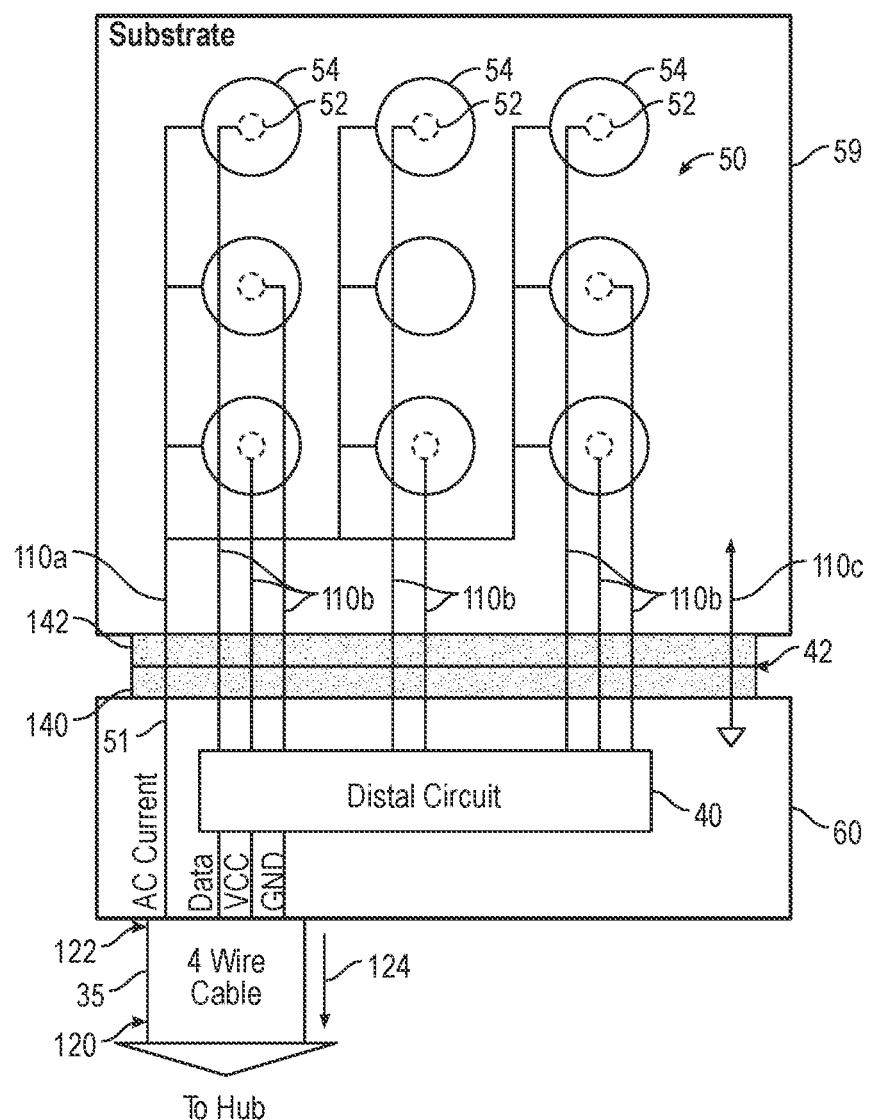

Referring to FIGS. 4A-4C, in some embodiments, the one or more transducer arrays 50 may be sterilized before use (e.g., via radiation and/or gas). As the distal circuit 40 is located between the connector 42a and the hub 30, the portion of the system 10 that includes the distal circuit 40 may not require sterilization. This permits sterilization of the transducer arrays 50 (e.g., using gas and/or radiation) without risk of damage to the distal circuit 40.

In some embodiments, a plurality of signals 110 may traverse the connector 42. For example, in FIG. 4B, ten signals 110 may traverse the connector 42 with one signal 110a for the AC current to the one or more electrode elements 52; one signal 110b for each of the temperature sensors 54 (e.g., subtotal of eight); and, one signal 110c for a common ground that may be used for all of the temperature sensors 54.

In some embodiments, a substrate 59 may support one or more of the electrode elements 52 (see FIG. 4C). The one or more electrode elements 52 may be positioned on and/or against a body of a patient (e.g., head). The substrate 59 may be configured to hold and/or affix the one or more electrode elements 52 against the body of the patient. The one or more temperature sensors 54 may be positioned adjacent to and/or beneath respective electrode elements 52 such that the one or more temperature sensors 54 are configured to sense temperature of the electrode elements 52.

A cable 35 has a first end 120 and a second end 122. The cable 35 may include (i) a conductor 51 that permits current (e.g., AC current) to flow between the first end 120 of the cable 35 and the second end 122 of the cable 35; and, (ii) a data path 124 configured to carry digital data corresponding to temperature readings originating in the distal circuit 40 from the second end 122 of the cable 35 to the first end 120 of the cable 35 (i.e., in the direction of the hub 30).

In some embodiments, a module 60 may be mounted (e.g., either directly or through intervening components) to the second end 122 of the cable 35. The distal circuit 40 may be mounted in the module 60. In some embodiments, power (voltage, VCC) and ground (GND) for the distal circuit 40 may be provided via the cable 35.

A first portion 140 of the connector 42a may be provided at or on the module 60, and a second portion 142 of the connector 42a may be provided at or on the substrate 59. The first portion 140 of the connector 42a mates with the second portion 142 of the connector 42a such that electrical signals are configured to pass through the connector 42a from the transducer array 50 to the distal circuit 40 and then the hub 30. To that end, when the first portion 140 of the connector 42a is mated to the second portion 142 of the connector 42a, signals from the one or more temperature sensors 54 are configured to travel through wiring on the substrate 59, through the connector 42a, and into the distal circuit 40. The distal circuit 40 includes the multiplexer 81, the analog to digital converter 83, and the controller 85. In addition, the common ground signal 110c for the one or more temperature sensors 54 may be provided through the connector 42a, in addition to, AC current signal 110a for the electrode elements 52. The AC current signal 110a may continue through appropriate wiring on the substrate 59 such that the one or more electrode elements 52 may be electrically connected to a corresponding conductor of the cable 35.

Referring to FIGS. 4C and 4D, in some embodiments, the signals 110a-110c may pass through the connector 42a via conductive elements within the connector 42a. The conductive elements may include the plurality of pins 200 such that the first portion 140 of the connector 42a is matingly connected to the second portion 142. In some embodiments, one or more pins 200 may be provided on the first portion 140 of the connector 42a to matingly connect to conductive elements on the second portion 142 of the connector 42a. In some embodiments, one or more pins 200 may be provided on the second portion 142 of the connector 42a to matingly connect to conductive elements on the first portion 140 of the connector 42a.

Figure 4F:
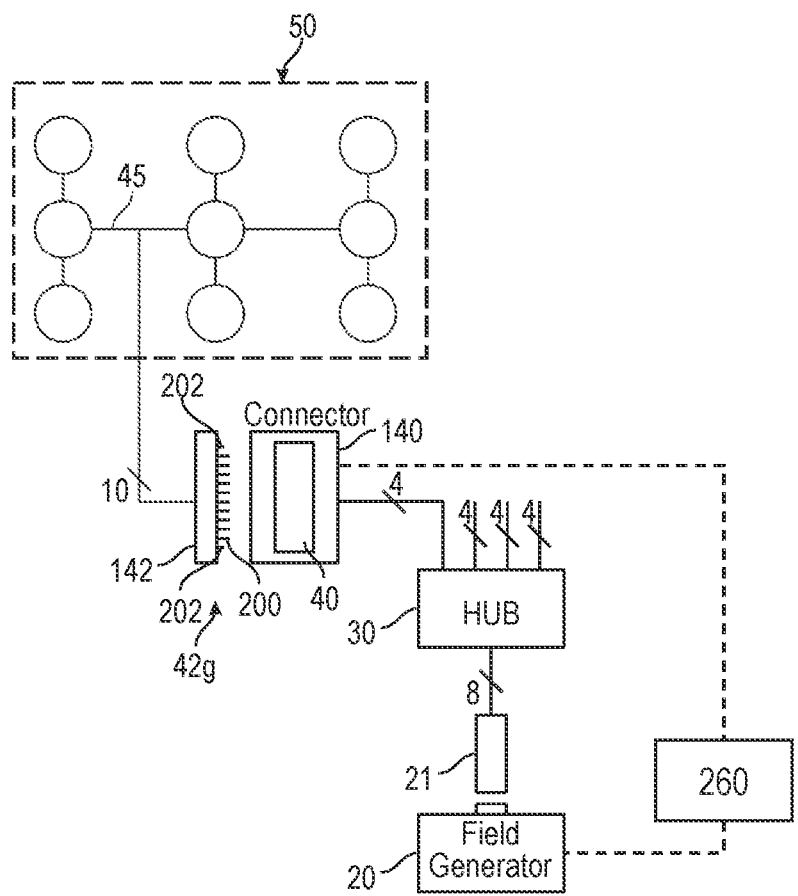

In some embodiments, the connector 42a may include one or more indicator pin(s) 202 in addition to pins 200. The one or more indicator pin(s) 202 may be integrated into the connector 42a at the first portion 140 and/or the second portion 142 of the connector 42a. In some embodiments, one or more indicator pin(s) 202 may be integrated on the same one of the first portion 140 or second portion 142 of the connector 42a as the pins 200. In some embodiments, one or more indicator pin(s) 202 may be integrated on a different one of the first portion 140 or the second portion 142 of the connector 42a as compared to the pins 200. For example, the pins 200 can be non-removably mounted to the first portion 140, and the indicator pin(s) 202 can be non-removably mounted to the second portion 142. FIG. 4F illustrates another exemplary embodiment of the connector 42a wherein the electrical connectors 200 (e.g., pins) and indicator electrical connectors 202 (e.g., indicator pins) may be non-removably mounted to the second portion 142, shown as a connector 42g.

The connector 42a may include a first end 204 and a second end 206 (FIGS. 4D and 4E). In some embodiments, one or more indicator pin(s) 202 may be positioned at the first end 204 and/or the second end 206 of the connector 42a. In some embodiments, at least one indicator pin 202 may be positioned at the first end 204 of the connector 42a and at least one indicator pin 202 may be positioned at the second end 206 of the connector 42a. In some embodiments, one indicator pin 202 may be positioned at the first end 204 of the connector 42a, or the one indicator pin 202 may be positioned at the second end 206 of the connector 42a. For clarity and conciseness, exemplary embodiments illustrate a single indicator pin 202 (see FIG. 4D) or two indicator pins 202a and 202b (see FIG. 4E), however, any number of indicator pins 202 may be used and are contemplated within the present disclosure.

Because signals 110b provided from the temperature sensors 54 may be influenced by changes associated with salt water (e.g., sweat from a patient within the connector 42a may result in higher temperature reading data from the measured data), in some embodiments, the first portion 140 and the second portion 142 of the connector 42a may generally be formed of waterproof material (e.g., rubber) to prevent moisture (e.g., perspiration, showers, etc.) from interfering with the electric circuitry including the pins 200 and the indicator pin(s) 202. Further, the first portion 140 and the second portion 142 may be configured to mate together to form a waterproof seal that protects the pins 200 and the indicator pin(s) 202 from intrusion from water external to the first portion 140 and the second portion 142. Additionally, the intrusion of non-salt water and/or salt water may indicate disconnection (or lack of full waterproof connection) between the first portion 140 and the second portion 142 of the connector 42a. The one or more indicator pin(s) 202 may provide feedback regarding status of the connector 42a. Status may be one or more conditions of the connector 42a during use of the system 10. Conditions may include, but are not limited to, lack of connection, presence of water, presence of salt, presence of one or more external substances, disconnection of the first portion 140 from the second portion 142, combinations thereof and the like. To that end, in some embodiments, the indicator pin(s) 202 may aid in detection of disconnection of the first portion 140 of the connector 42a to the second portion 142 of the connector 42a, for example. In some embodiments, the indicator pin(s) 202 may aid in detection of voltage loss, loss of current, and/or the like between the first portion 140 of the connector 42a and the second portion 142 of the connector 42a, for example.

Referring to FIG. 4D, one or more pins 200 on the first portion 140 of the connector 42a may matingly connect to one or more socket connectors 212a on the second portion 142 of the connector 42a. Similarly, one or more indicator pin(s) 202 on the first portion 140 of the connector 42a may matingly connect to one or more indicator socket connectors 212b on the second portion 142 of the connector 42a. The pins 200, the indicator pin(s) 202, the socket connectors 212a, and the indicator socket connector(s) 212b are constructed of or coated with a conductive material, such as copper, aluminum, gold, silver, and combinations thereof. In some embodiments, depth $d_p$ of the socket connector 212a associated with the respective pin 200 may be similar to depth $d_I$ of the indicator socket connector 212b associated with the respective indicator pin 202. In some embodiments, depth $d_p$ of the socket connector 212a associated with the respective pin 200 may be configured to be greater than depth $d_I$ of the indicator socket connector 212b associated with the respective indicator pin 202 such that disconnection between the one or more indicator pin(s) 202 and the indicator socket connector(s) 212b may occur prior to disconnection of the pins 200 from the socket connectors 212a. Monitoring connection or disconnection of the one or more indicator pin(s) 202 and the indicator socket connector(s) 212b permits detection of partial disconnection and therefore possible and/or probable disconnection (or imminent disconnection) of the first portion 140 from the second portion 142.

In some embodiments, the one or more indicator pin(s) 202 may have a length $L_I$ similar to length $L_P$ of the pins 200. In some embodiments, the length $L_I$ of the one or more indicator pin(s) 202 may be shorter than the length $L_P$ of the pins 200 such that disconnection between the one or more indicator pin(s) 202 and the associated indicator socket connector 212b may occur prior to disconnection of the pins 200 and associated socket connector 212a and/or one or more indicator pin(s) 202 may be configured to provide detection of possible and/or probable disconnection of the first portion 140 from the second portion 142.

Referring to FIG. 4D, in some embodiments, the one or more indicator socket connectors 212b may be in electrical communication with one or more resistors $R_I$. Current can be supplied to the one or more indicator socket connector(s) 212b from the indicator pin 202. Current may be provided by controller 85, distal circuit 40, hub 30, electric field generator 20, an external source, or combinations thereof. In some embodiments, the resistor $R_I$ may be the precision resistor 89 described herein. In some embodiments, the resistor $R_I$ may be one or more separate resistors. An electrical parameter, such as voltage across the one or more resistors $R_I$, may be monitored by an instrument 213 to determine status of the connector 42a. The voltage across the one or more resistor(s) $R_I$ may be monitored and/or logged at a plurality of instances of time with the instrument 213 to detect changes in the electrical parameter, such as voltage across the resistor $R_I$. For example, once the indicator pin 202 is matingly engaged and/or matingly connected with the indicator socket connector 212b, changes in voltage across the resistor $R_I$ may indicate salt water entering between the first portion 140 and the second portion 142 of the connector 42a. In some embodiments, a calibrated voltage across the resistor $R_I$ may be determined. Variations from the calibrated voltage may indicate a different status of the connector 42a (e.g., salt water present, disconnected first portion 140 and second portion 142). Complete voltage loss to the resistor $R_I$ may indicate disconnection of the first portion 140 from the second portion 142.

Referring now to FIG. 4E, shown therein is a diagram of an exemplary embodiment of a connector 42b constructed in accordance with the construction of the connector 42a with the exception that, in some embodiments, two or more indicator pins 202 (shown in FIG. 4E as indicator pin 202a and indicator pin 202b) may form one or more monitoring circuits 210 (e.g., simple circuit, series circuit) across a first portion 140b of a connector 42b and a second portion 142b of the connector 42b. In some embodiments, the indicator pins 202 may be positioned on the first portion 140b of the connector 42b and corresponding indicator socket connectors 212b may be positioned on the second portion 142b of the connector 42b. One or more conductive lines 214 may be provided between indicator socket connectors 212b. Current may be provided by controller 85, distal circuit 40, hub 30, electric field generator 20, an external source, or combinations thereof. To that end, when the indicator pins 202a, 202b are matingly engaged within the indicator socket connectors 212b, a monitoring circuit 210 (e.g., closed circuit) may be formed.

Although the monitoring circuit 210 is described herein as being a closed circuit, it should be understood that the monitoring circuit 210 can be implemented in other manners to determine the status of the connector 42b. Exemplary status includes relative locations of the first portion 140b and the second portion 142b to determine whether the first portion 140b and the second portion 142b are connected or disconnected. The monitoring circuit 210 may monitor one or more electrical sensors, optical sensors, or mechanical mechanisms to determine the relative locations and/or orientation of the first portion 140b and the second portion 142b. Exemplary electrical sensors include inductive proximity sensors, magnetic proximity sensors, or capacitive proximity sensors. In each of these electrical sensors, a sensor can be mounted on one of the first portion 140b and the second portion 142b, and a detection object may be mounted on the other one of the first portion 140b and the second portion 142b. Optical sensors may include a photosource (e.g., photodiode) mounted to one of the first portion 140b and the second portion 142b, and an optical detector (e.g., photodiode) mounted to the other one of the first portion 140b and the second portion 142b. In other embodiments, the photosource and the optical detector can be mounted to either one of the first portion 140b or the second portion 142b, and a reflector can be mounted to the other one of the first portion 140b and the second portion 142b. Examples of mechanical mechanisms, such as the one or more indicator pin(s) 202 and indicator socket connectors 212b monitored by the monitoring circuit 210 are described in detail herein. If one or more indicator pin(s) 202a, 202b become disconnected from the indicator socket connectors 212b, the monitoring circuit 210 is broken and current does not flow through the second portion 142 of the connector 42b. Monitoring for changes in current along the monitoring circuit 210 (e.g., by the controller 85) may provide status of the connector 42b.

In some embodiments, the monitoring circuit 210 may include one or more resistors $R_I$. Similar to the exemplary embodiment in FIG. 4D, voltage across the one or more resistors $R_I$ may be monitored to determine status of the connector 42b. For example, changes in voltage across the resistor $R_I$ may indicate salt water entering between the first portion 140 and the second portion 142 of the connector 42b. In some embodiments, a calibrated voltage across the resistor $R_I$ may be determined. Variations from the calibrated voltage may indicate a different status of the connector 42b (e.g., salt water present, disconnected first portion 140 and second portion 142). Complete voltage loss to the resistor $R_I$ may indicate disconnection of the first portion 140 from the second portion 142.

Referring to FIGS. 1, 4D, and 4E, in some embodiments, an indicator system 260 is provided with circuitry that may be configured to provide data, status, conditions, actions, commands or combinations thereof to a user and/or patient. For example, in some embodiments, the indicator system 260 may provide data associated with the status of one or more components of the system 10 (e.g., on/standby, error indications, status of battery charge, compliance metrics). In some embodiments, the indicator system 260 may be mounted at any point along the cable 25 between the hub 30 and the electric field generator 20. In some embodiments, the indicator system 260 may be mounted to the hub 30. In some embodiments, the indicator system 260 may be mounted at the distal circuit 40. In some embodiments, the indicator system 260 may be mounted at the controller 85. In some embodiments, the indicator system 260 may be integrated within the connector 42, within the hub 30, within the electric field generator 20, within the controller 85 and/or combinations thereof.

In some embodiments, the indicator system 260 may perform or cause the performance of a predetermined action such as providing visual, auditory and/or haptic feedback to the user regarding status of the connector 42 based upon receipt of one or more signals generated by the monitoring circuit 210. The indicator system 260 may receive data regarding variation in voltage and/or variation in current provided via use of the indicator pin(s) 202. Data regarding variation in voltage and/or variation in current provided via use of the indicator pin(s) 202 may provide one or more feedback commands to a user. One or more feedback commands may be provided via visual system (e.g., LED light, screen, monitor, and/or the like), auditory (e.g., tone, buzz) or haptic system (e.g., vibration). Feedback commands, also referred to as an associative action, may include, but are not limited to, "Take connector apart", "Dry connector", "Apply force to connector", and/or the like. For example, the visual system may provide a red light indicating the status of the connector 42 is poor and commanding the user to "Take apart connector" or "Push connector together." In another example, the visual system may provide a green light indicating the status of the connector 42 is good and commanding the user to "Continue using the system". As described herein, the system may be configured to signal the electric field generator to power down. For example, detection of disconnection of indicator pins from indicator socket connectors could be used as a safety mechanism to power down the electric field generator.

FIG. 5A-5E, illustrate exemplary embodiments of the connector 42 positioned between the distal circuit 40 and the hub 30 such that signals 250 from the distal circuit 40 traverse the connector 42. For example, in FIG. 5B and FIG. 5C, four signals 250a-d traverse the connector 42c: a first signal 250a for the AC current that goes to the electrode elements 52 ("AC Current"), a second signal 250b for data that travels between the UART 86 and the hub 30 ("Data"); a third signal 250c for power to the distal circuit 40 ("VCC"), and a fourth signal 250d for ground for the distal circuit 40 ("GND").

Figure 5A:
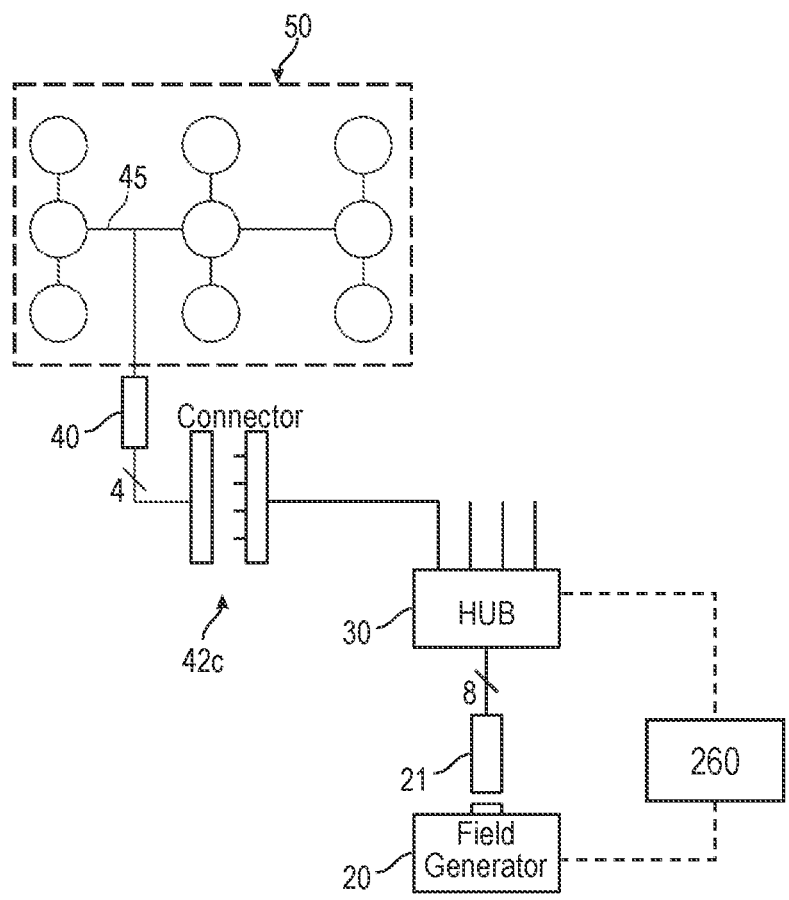
Figure 5B:
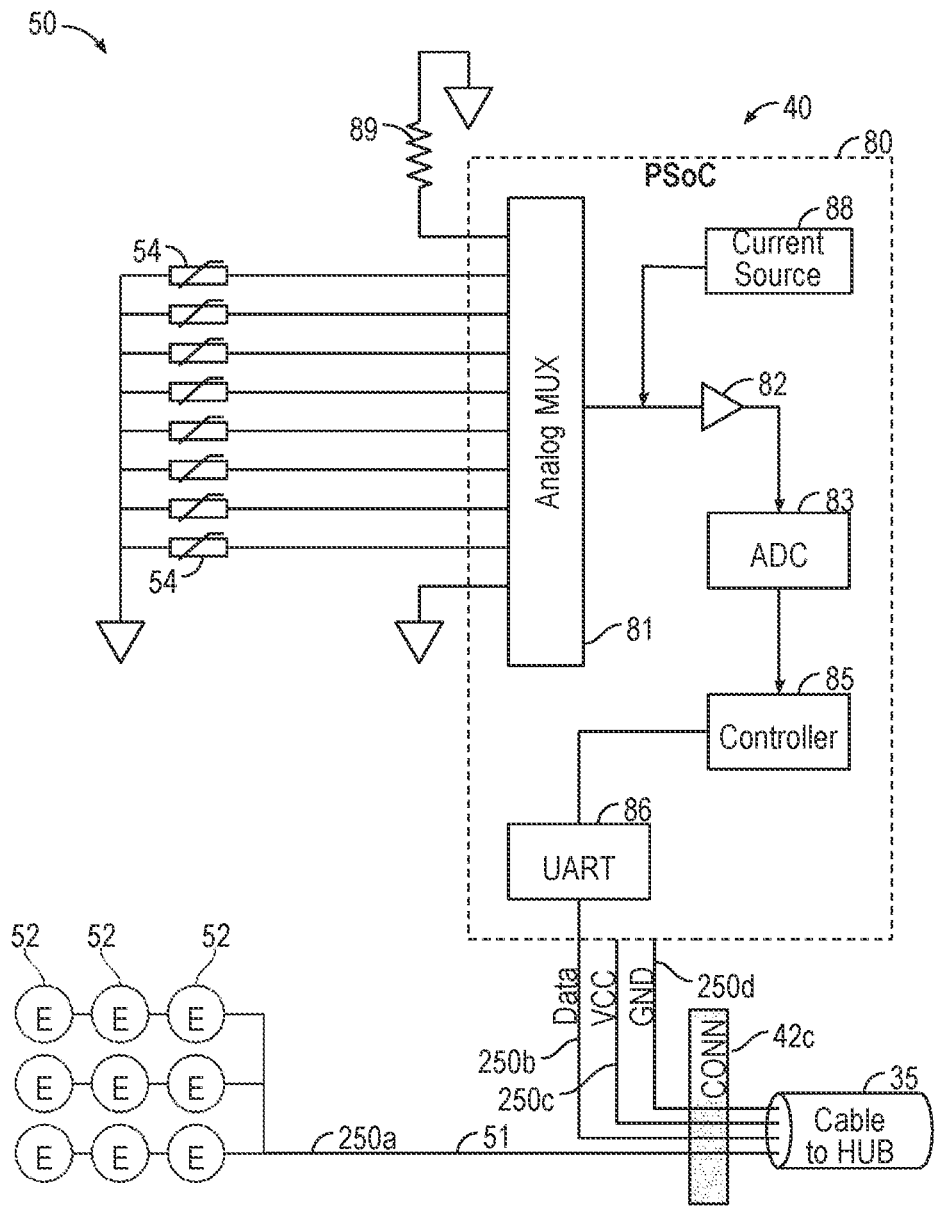
Figure 5C:
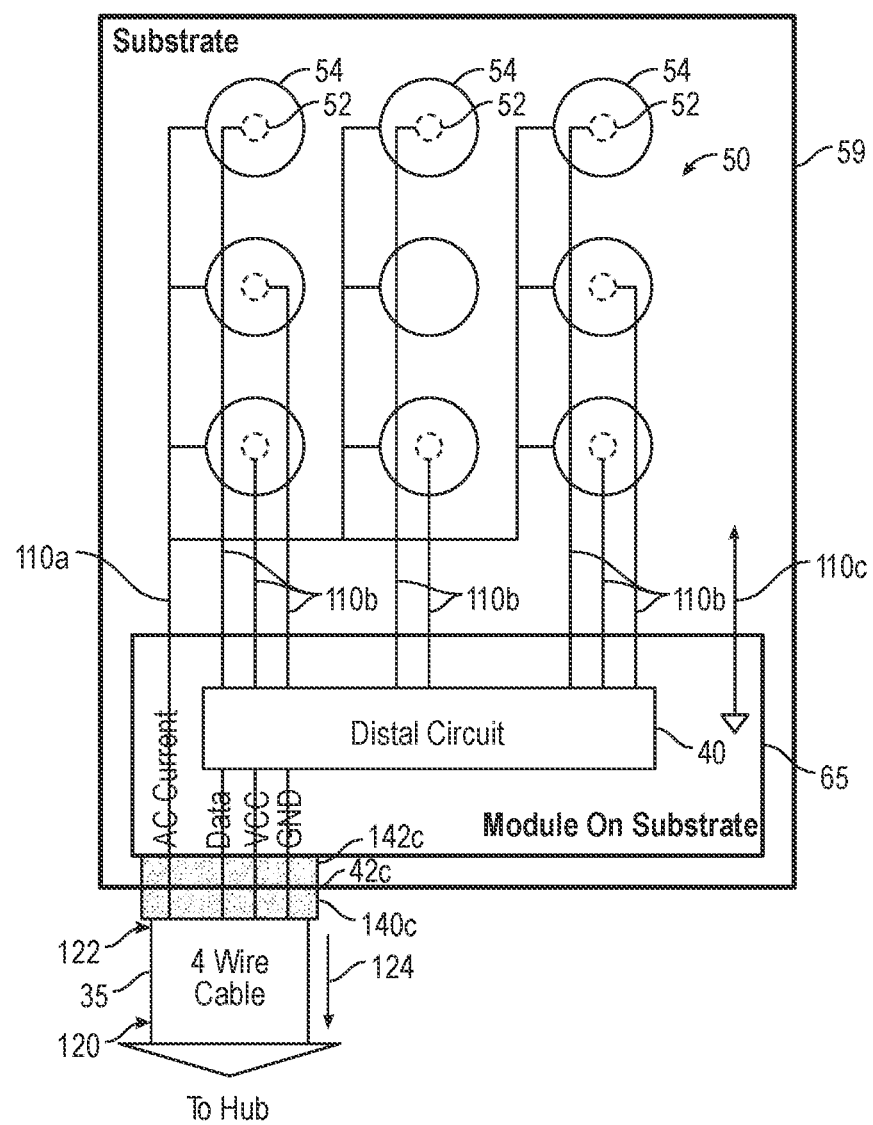

Referring to FIGS. 5B and 5C, the substrate 59 may support the one or more electrode elements 52. The one or more electrode elements 52 may be configured for placement against the body of the patient (e.g., head), and/or the substrate 59 may be configured to hold the plurality of electrode elements 52 against the body of the patient. The one or more temperature sensors 54 may be positioned adjacent to and/or beneath respective electrode elements 52 such that the one or more temperature sensors 54 can sense the temperature of the electrode elements 52.

A module 65 may be mounted (either directly or through intervening components) to the substrate 59. In some embodiments, the distal circuit 40 may be mounted in the module 65. In some embodiments, power (voltage, VCC) and ground (GND) for the distal circuit 40 may be provided via cable 35. The first portion 140c of the connector 42c is provided at the second end 122 of the cable 35, and the second portion 142c of the connector 42c is provided on the substrate 59. The first portion 140c of the connector 42c is matingly connected to the second portion 142c of the connector 42c such that electrical signals can pass through both portions 140c and 142c of the connector 42c. When both portions 140c and 142c of the connector 42c are mated, signals from the cable 35 may travel through the connector 42c, and into the distal circuit 40. Similarly, when both portions 140c and 142c of the connector 42c are mated, signals from the distal circuit 40 may travel through the connector 42c to the hub 30.

In some embodiments, the cables 35 may be disconnected from the substrate 59 when the one or more transducer arrays 50 are initially placed on the body of the patient. Once the one or more transducer arrays 50 are in a desired position, the cables 35 may be connected to the transducer arrays 50 via the connector 42c.

Referring to FIG. 5C and FIG. 5D, in some embodiments, similar to FIGS. 4C and 4D, the signals 250a-250d (shown in FIG. 5B) may be provided via a plurality of pins 200 such that the first portion 140c of the connector 42c is matingly connected and/or matingly engaged to the second portion 142c. In some embodiments, one or more pins 200 may be provided on the first portion 140c of the connector 42c to matingly connect to the second portion 142c of the connector 42c (shown in FIG. 5D). In some embodiments, one or more pins 200 may be provided on the second portion 142c of the connector 42c to matingly connect to the first portion 140c of the connector 42c.

In some embodiments, the connector 42c may include one or more indicator pin(s) 202 in addition to pins 200. The one or more indicator pin(s) 202 may be integrated into the connector 42c. In some embodiments, one or more indicator pin(s) 202 may be integrated on the same portion 140c or 142c of the connector 42c as the pins 200. In some embodiments, one or more indicator pin(s) 202 may be integrated on a different one of the first portion 140c or second portion 142c of the connector 42c as the pins 200. The connector 42c may include a first end 204c and a second end 206c. In some embodiments, one or more indicator pin(s) 202 may be positioned at the first end 204c and/or the second end 206c of the connector 42c. In some embodiments, at least one indicator pin 202 may be positioned at the first end 204c of the connector 42c and at least one indicator pin 202 may be positioned at the second end 206c of the connector 42c. In some embodiments, one indicator pin 202 may be positioned at the first end 204c of the connector 42c or positioned at the second end 206c of the connectors 42c. For clarity and conciseness, exemplary embodiments illustrating single indicator pin 202 (shown in FIG. 5D) and two indicator pins 202 (shown in FIG. 5E) are illustrated, however, any number of indicator pins 202 may be used and are contemplated within the present disclosure.

The one or more indicator pin(s) 202 may provide feedback regarding status of the connector 42c. To that end, in some embodiments, the indicator pin(s) 202 may aid in detection of disconnection or partial disconnection of the first portion 140c of the connector 42c to the second portion 142c of the connector 42c. In some embodiments, the indicator pin(s) 202 may aid in detection of voltage loss, loss of current, and/or the like between the first portion 140c of the connector 42c and the second portion 142c of the connector 42c.

Referring to FIG. 5D, one or more pins 200 on the first portion 140c of the connector 42c may matingly connect to one or more socket connectors 212a. Similarly, one or more indicator pin(s) 202 on the first portion 140c of the connector 42c may matingly connect to one or more indicator socket connectors 212b on the second portion 142c of the connector 42c. In some embodiments, depth $d_p$ of the socket connector 212a associated with the respective pin 200 may be similar to depth $d_I$ of the indicator socket connector 212b associated with the respective indicator pin 202. In some embodiments, depth $d_p$ of the socket connector 212a associated with the respective pin 200 may be configured to be greater than depth $d_I$ of the indicator socket connector 212b associated with the respective indicator pin 202 such that disconnection between the one or more indicator pin(s) 202 may occur prior to disconnection of the pins 200 and/or one or more indicator pin(s) 202 may be configured to provide detection of partial disconnection and therefore possible and/or probable disconnection of the first portion 140c from the second portion 142c.

In some embodiments, the length $L_I$ of the one or more indicator pin(s) 202 may be similar to length $L_P$ of the pins 200. In some embodiments, the length $L_I$ of the one or more indicator pin(s) 202 may be shorter than the length $L_P$ of the pins 200 such that disconnection between the one or more indicator pin(s) 202 from the associated indicator socket connector 212b may occur prior to disconnection of the pins 200 from the associated socket connector 212a and/or one or more indicator pin(s) 202 may be configured to provide detection of partial disconnection or possible and/or probable disconnection of the first portion 140c from the second portion 142c.

Referring to FIG. 5D, in some embodiments, the one or more indicator socket connectors 212b may be in electrical communication with one or more resistors $R_I$. In some embodiments, the resistor $R_I$ may be the precision resistor 89 described herein. In some embodiments, the resistor $R_I$ may be one or more separate resistors. Voltage across the one or more resistors $R_I$ may be monitored to determine status of the connector 42c. For example, once the indicator pin 202 is matingly connected and/or engaged with the indicator socket connector 212b, changes in voltage across the resistor $R_I$ may indicate salt water entering between the first portion 140c and the second portion 142c of the connector 42c. In some embodiments, a calibrated voltage across the resistor $R_I$ may be determined. Variations from the calibrated voltage may indicate a different status of the connector 42c (e.g., salt water present, disconnected first portion 140c and second portion 142c, partial disconnection). Complete voltage loss to the resistor $R_I$ may indicate disconnection of the first portion 140c from the second portion 142c.

Referring now to FIG. 5E, shown therein is a connector 42d constructed in accordance with the connector 42c, described above, with the exception that, in some embodiments, two or more indicator pins 202 may form one or more monitoring circuit 210a (e.g., simple circuit, series circuit) across a first portion 140d of the connector 42d and a second portion 142d of the connector 42d. In some embodiments, the indicator pins 202 may be positioned on the first portion 140d of the connector 42d and corresponding indicator socket connectors 212b may be positioned on the second portion 142d of the connector 42d. One or more conductive lines 214 may be provided between the indicator pins 202, or the indicator socket connectors 212b. In the embodiment shown in FIG. 5E, current may be provided by controller 85, distal circuit 40, hub 30, electric field generator 20, an external source, or combinations thereof. To that end, when the indicator pins 202 are matingly engaged within the indicator socket connectors 212b, a monitoring circuit 210a (i.e., closed circuit) may be formed. If one or more indicator pins 202 become disconnected from the indicator socket connectors 212b, the monitoring circuit 210a is broken and current does not flow through the second portion 142d of the connector 42d. Monitoring for changes in current along the monitoring circuit 210a may provide status of the connector 42d by disconnecting the one or more indicator pin(s) 202 from the associated indicator socket connector 212b prior to disconnection of the pins 200 from the associated socket connectors 212a (e.g., a partial disconnection).

Figure 5F:
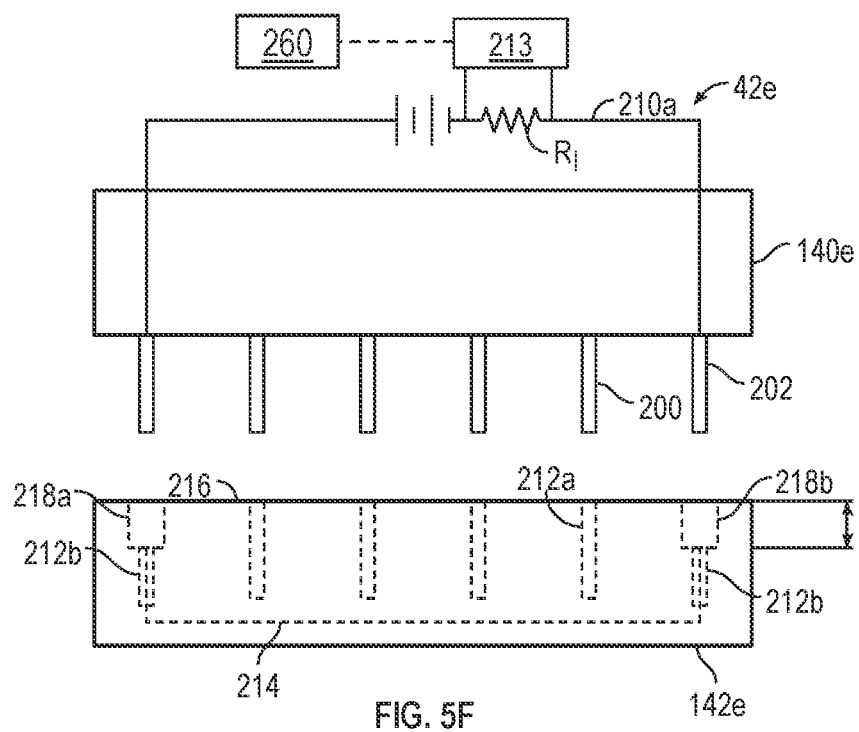

Referring to FIG. 5F, shown therein is another example of a connector 42e constructed in accordance with the present disclosure. The connector 42e includes a first portion 140e and a second portion 142e. The connector 42e is similar in construction and function as the connector 42d described above with the exception that the indicator pins 202 are a same length as the pins 200, but the indicator socket connectors 212b are recessed within the second portion 142e. In particular, the second portion 142e is provided with a first side 216 adjacent to the socket connectors 212a and the indicator socket connectors 212b. The socket connectors 212a may extend through the first side 216. The first side 216 is configured to mate against the first portion 140e such that the pins 200 can extend into socket connectors 212a and the indicator pins 202 extend into the indicator socket connectors 212b. Opening(s) 218a and 218b can be provided between the first side 216 and the indicator socket connectors 212*b* to permit the indicator pins 202 to pass into and engage with the indicator socket connectors 212*b*. The socket connectors 212*a* may be flush with the first side 216 (or spaced a first distance from the first side 216), and the indicator socket connectors 212*b* may be spaced a second distance 220 from the first side 216. The second distance 220 is greater than the first distance that the socket connectors 212*a* are spaced from the first side 216 to cause disconnection of the indicator socket connectors 212*b* from the indicator pins 202 prior to disconnection of the pins 200 from the socket connectors 212*a*. In some embodiments, two or more indicator pins 202 may form one or more monitoring circuits 210*a* (e.g., simple circuit, series circuit) across the first portion 140*e* of the connector 42*e* and the second portion 142*e* of the connector 42*e*.

In some embodiments, the indicator pins 202 may be connected to the first portion 140*e* of the connector 42*e* and corresponding indicator socket connectors 212*b* may be connected to the second portion 142*e* of the connector 42*e*. One or more conductive lines 214 may be provided between indicator socket connectors 212*b* within the second portion 142*e*. Current may be provided by controller 85, distal circuit 40, hub 30, electric field generator 20, an external source, or combinations thereof. To that end, when the indicator pins 202 are matingly engaged within the indicator socket connectors 212*b*, a monitoring circuit 210*a* (i.e., closed circuit) may be formed. If one or more indicator pins 202 become disconnected from the indicator socket connectors 212*b*, the monitoring circuit 210*a* is broken and current does not flow through the second portion 142*e* of the connector 42*e*. Monitoring for changes in current along the monitoring circuit 210*a* may provide status of the connector 42*e* by disconnecting the one or more indicator pin(s) 202 from the associated indicator socket connector 212*b* prior to disconnection of the pins 200 from the associated socket connectors 212*a* (e.g., a partial disconnection).

Referring to FIGS. 5D, 5E and 5F, in some embodiments, an indicator system 260 (as described above for FIGS. 4D and 4E) is provided with circuitry that may be configured to provide data, status, conditions, actions, commands or combinations thereof to a user and/or patient.

Figure 5G:
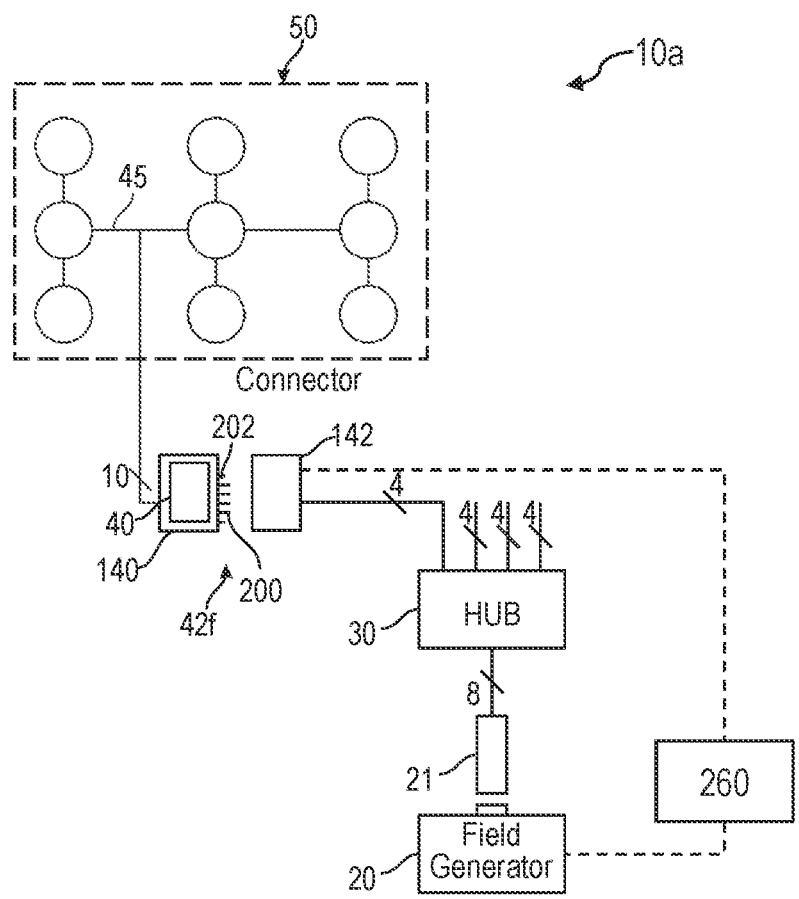

Referring now to FIG. 5G, shown therein is an exemplary embodiment of a system 10*a* constructed in accordance with the present disclosure. The system 10*a* is constructed similar to the system of FIG. 4A with the exception that the connector 42*a* is reversed and shown as connector 42*f* having only four (4) electrical connectors 200 and at least one of the single indicator pin 202. The connector 42*f* includes the first portion 140 having the first distal circuit 40 integrated therein and the second portion 142. The first portion 140, having the first distal circuit 40, receives each of the signal 110*b*, and processes each of signal 110*b* into the signals 250*a-d*. As discussed above (referring to FIG. 5B and FIG. 5C), the four signals 250*a-d* traverse the connector 42*f*: the first signal 250*a* for the AC current that goes to the electrode elements 52, the second signal 250*b* for data that travels between the UART 86 and the hub 30; the third signal 250*c* for power to the distal circuit 40, and the fourth signal 250*d* for ground for the distal circuit 40.

An exemplary method for using the system 10 in accordance with the present disclosure is herein described. In a first step, one or more electrode elements 52 may be affixed to a body of a patient. In a second step, one or more pins 200 may be matingly connected to one or more socket connectors 212*a*. Additionally, one or more indicator pins 202 may be matingly connected to one or more indicator socket connectors 212*b*. In a third step, current may be provided to one or more indicator pins 202. In a fourth step, the controller 85, hub 30, electric field generator 20, or combinations thereof may monitor feedback from the current provided to the one or more indicator pins 202 during use of the system 10 via instrument 213 in obtaining one or more temperature readings and providing TTFields. For example, the controller 85 may monitor changes in voltage across one or more resistor $R_I$ to monitor feedback from the current provided to the one or more indicator pins 202 as described herein. In a fifth step, the hub 30, or the electric field generator 20 may determine status of the connector 42 based on feedback from the current provided to the one or more indicator pins 202. For example, if the voltage is at 0, the determination of the status of the connector 42 may be that the first portion 140 of the connector 42 is disconnected from the second portion 142 of the connector 42. In a sixth step, one or more indicators, and, optionally, actions, commands, data, or combinations thereof may be provided to a user and/or the patient. For example, the one or more indicators may provide status of the connector 42 and/or provide recommended actions appropriate to ensure continued use of the connector 42.

Optionally, if disconnection or partial disconnection is detected, a signal from the monitoring circuit 210 or the indicator system 260 may be sent to the electric field generator 20 to effect the predetermined action, such as powering down of the electric field generator 20. The electric field generator 20 may be provided with a power-down circuit configured to receive the signal and cause the powering down of the electric field generator 20. The power down circuit can be an analog to digital converter coupled to an interface of a microprocessor, or a relay.

In some embodiments, an optional step may include disconnecting the first portion 140 of the connector 42 and the second portion 142 of the connector 42 (i.e., pins 200 may be disconnected from socket connectors 212*a* and indicator pins 202 may be disconnected from indicator socket connectors 212*b*), such that the electrode elements 52 may be sanitized and/or cleaned. The first portion 140 of the connector 42 may then be reconnected to the second portion 142 of the connector 42.

Figure 6:
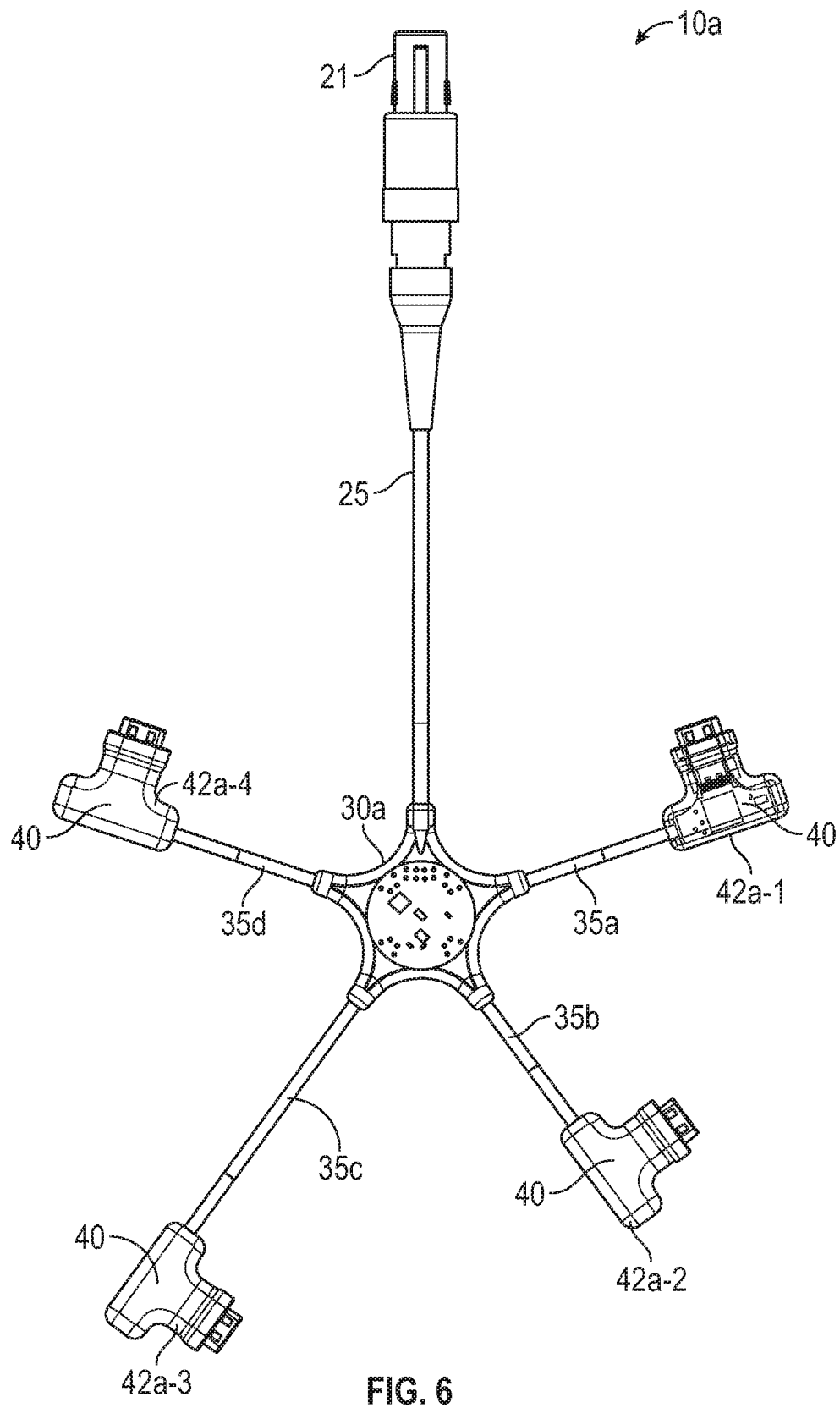
FIG. 6 is a diagram of an exemplary embodiment of a system constructed in accordance with the present disclosure and having a plurality of connectors.

Referring now to FIG. 6, shown therein is a diagram of an exemplary embodiment of the system 10*a* constructed in accordance with the present disclosure. The system 10*a* includes a signal connector 21 as an electric field generator connector operable to connect the cable 25 to the electric field generator 20. As shown in FIG. 6, the cable 25 may be an 8-conductor cable electrically coupled to a hub 30*a*. In this embodiment, the hub 30*a* may function as a junction box operable to connect each transducer array 50 to the electric field generator 20. As shown, the hub 30*a* includes four cables 35 (i.e., cables 35*a-d*) connected to four connectors 42*a*-1 to 42*a*-4. In some embodiments, the connectors 42*a*-1-42*a*-4 are similar in construction and function as the connector 42*a*, however, the connectors 42*a*-1-42*a*-2 may be similar in construction and function as one of the connector 42*b* or the connector 42*g*.

In one embodiment, as shown in FIG. 6, the connectors 42*a*-1 to 42*a*-4 include the distal circuit 40 integrated with each of the connectors 42*a*-1 to 42*a*-4. Each connector 42*a*-1 to 42*a*-4 includes at least 10 pins 200 as discussed above. Each of the four cables 35 may be a four-wire cable between a particular connector 42*a* and the hub 30*a*. In one embodiment, each of the connectors 42*a*-1 to 42*a*-4 is a USB Type-C connector having at least 24 pins. In one embodiment, the USB Type-C connector is configured to be reversable, that is, the USB Type-C connector is configured to be coupled in either possible orientation.

Figure 7:
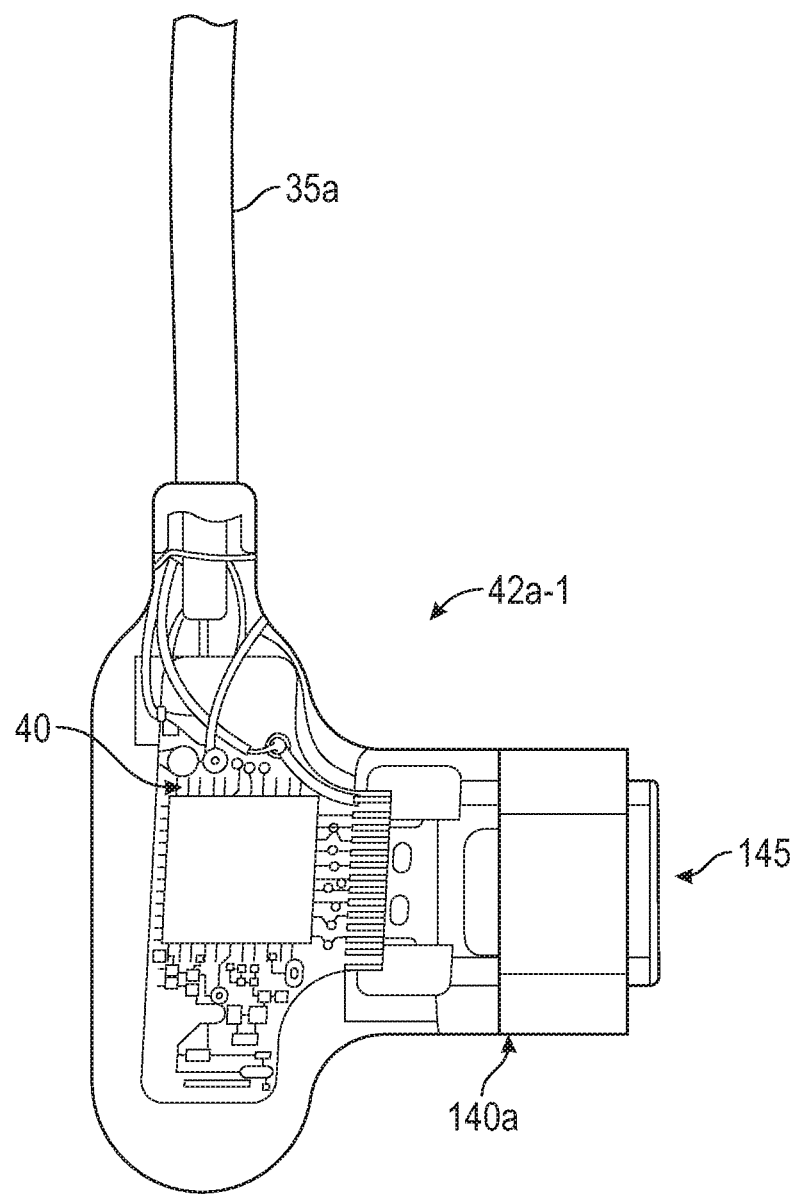
FIG. 7 is a diagram of an exemplary embodiment of one of the connectors of FIG. 6 constructed in accordance with the present disclosure.

Referring now to FIG. 7, shown therein is a diagram of an exemplary embodiment of the connector 42*a*-1. The connectors 42*a*-1-42*a*-4 may be identical in construction. Thus, only the connector 42*a*-1 will be described hereinafter for purposes of brevity. As shown, the connector 42*a*-1 is electrically coupled to the cable 35 and includes a first portion 140*a*. In one embodiment, the connector 42*a*-1 may use a common or standard connector form, such as a USB Type-C (USB-C) connector and the first portion 140*a* may be a USB-C port operable to receive a USB-C plug. In one embodiment, both the first portion 140*a* and a second portion 142*a* (shown in FIG. 8) are a USB-C port operable to receive a USB-C plug, and an intermediary connector 145 comprising two USB-C plugs may be used to couple the second portion 142*a* with the first portion 140*a*. In one embodiment, a USB-C connector and wire can be used in place of both the cables 35 and the cable 25.

In one embodiment, each of the USB Type-C connector is a watertight connector. For example, the USB Type-C connector as the watertight connector may include a gasket between the first portion 140 and the second portion 142, such that when the first portion 140 is mated to the second portion 142 the gasket is compressed, creating a watertight seal between the first portion 140 and the second portion 142 thereby preventing contaminants, such as water, from penetrating the watertight seal and contacting the one or more pin 200, indicator 202, or socket 212.

Figure 8:
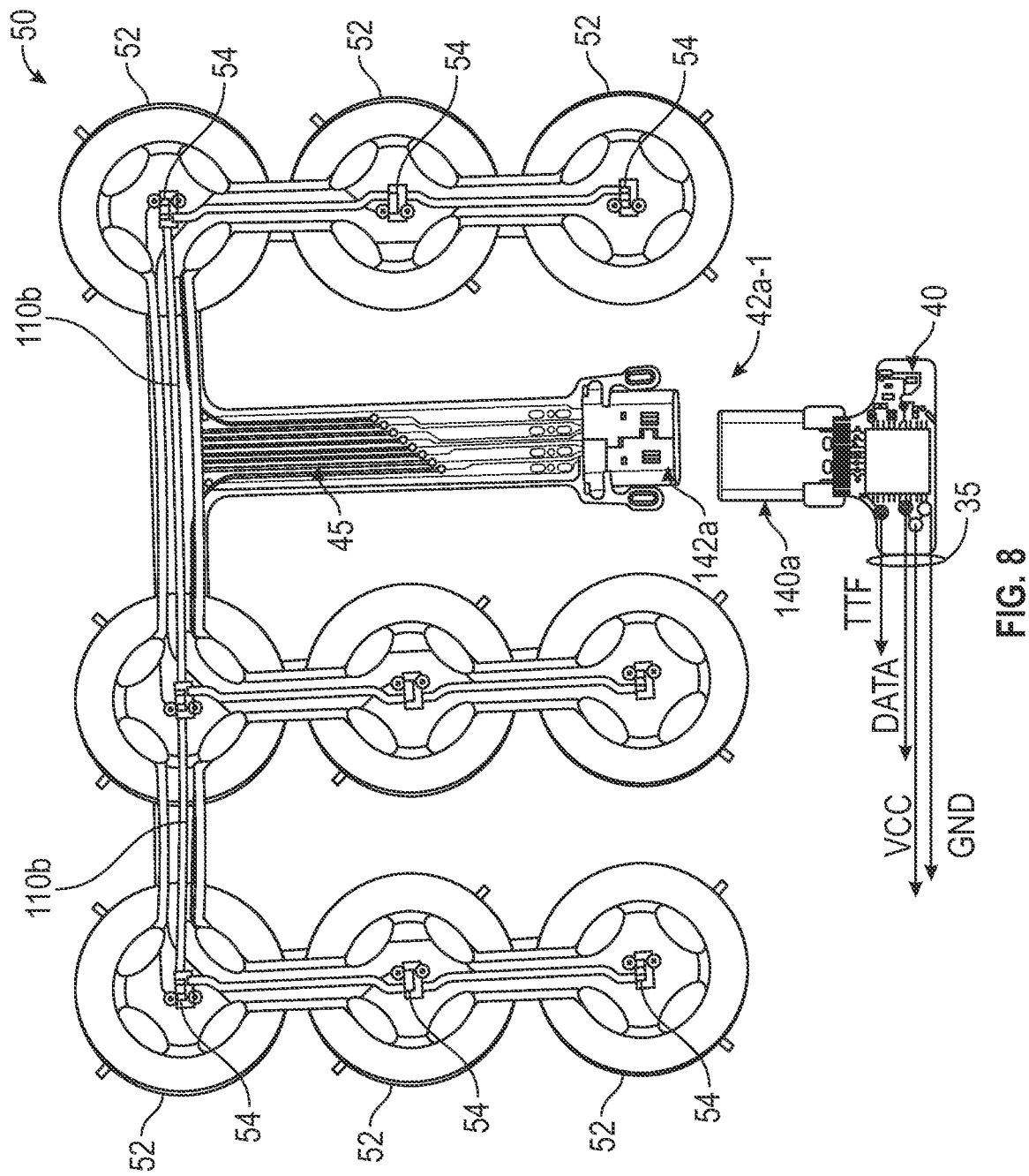
FIG. 8 is a top-down perspective of an exemplary embodiment of the connector of FIGS. 6-7 and the transducer array constructed in accordance with the present disclosure.

Referring now to FIG. 8, shown therein is a top-down perspective view of an exemplary embodiment of the connector 42*a*-1 and the transducer array 50 constructed in accordance with the present disclosure. The transducer array 50 includes a plurality of electrode elements 52 each associated with a particular temperature sensor 54. A plurality of wires 45 conduct signals 110*b* from the respective temperature sensor 54 of each electrode elements 52 to the second portion 142*a* of the connector 42*a*-1. The distal circuit 40 processes the plurality of signals 110*b* into a DATA signal and transmits the DATA signal along one of four conductors 51, e.g., GND, VCC, DATA, and TTF, of a 4-wire cable 35 as discussed above in more detail.

A plurality of wires 45 extend to the plurality of electrode elements 52. The plurality of wires 45 is shown as ten (10) wires 45 extending from the plurality of electrode elements 52 to the second portion 142*a* of the connector 42*a*-1. In one embodiment, as shown in FIG. 8, the distal circuit 40 is embedded into circuitry within the first portion 140*a* of the connector 42*a*-1 and is coupled to the cable 35, e.g., a 4-wire cable.

Figure 9:
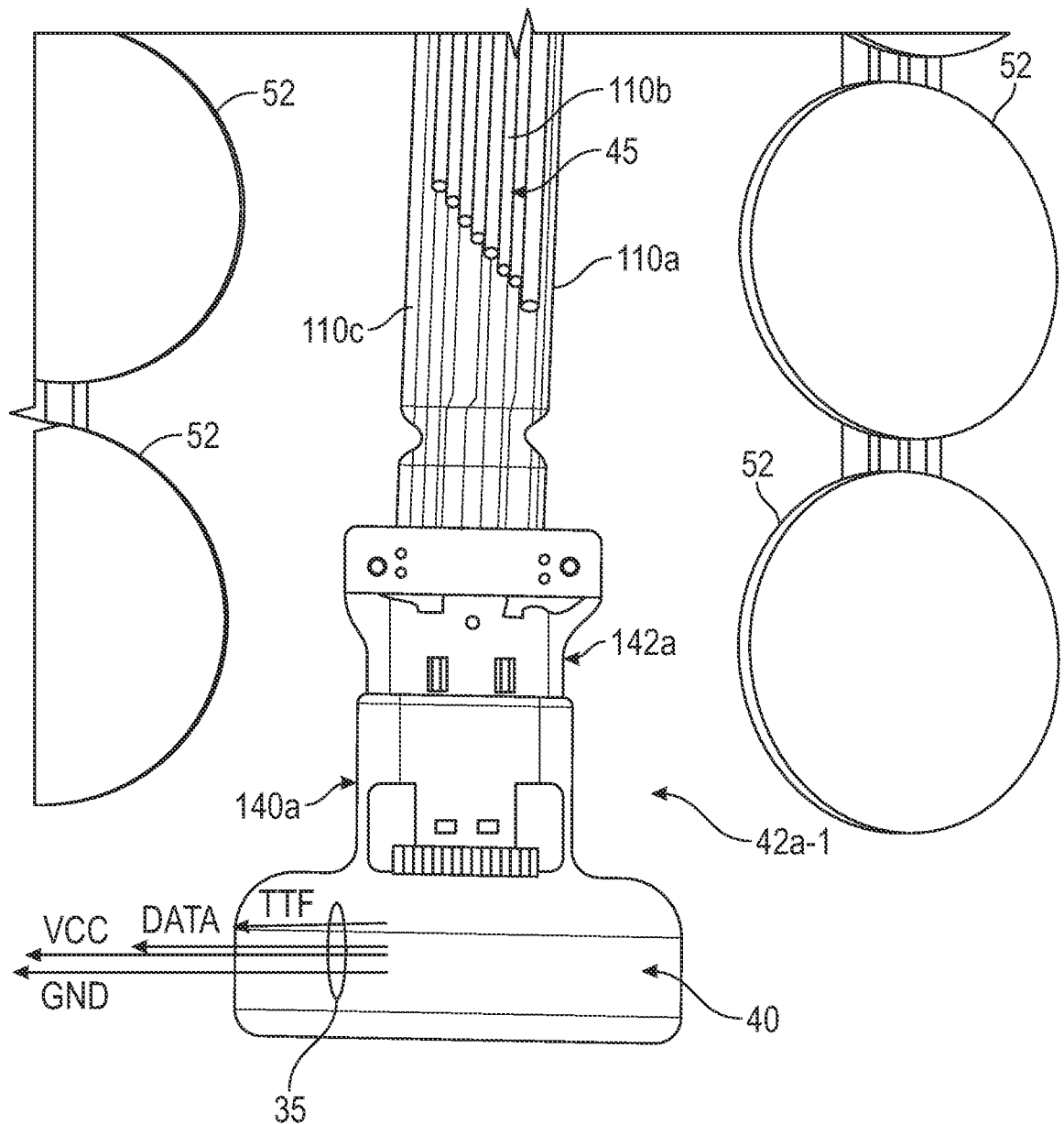
FIG. 9 is a bottom-up perspective of an exemplary embodiment of the connector and the transducer array of FIG. 8 constructed in accordance with the present disclosure.

Referring now to FIG. 9, shown therein is a bottom-up perspective view of an exemplary embodiment of the connector 42*a*-1 and the transducer array 50 of FIG. 8 constructed in accordance with the present disclosure. The transducer array 50 includes a plurality of electrode elements 52 each associated with a particular temperature sensor 54 not visible from this perspective. A plurality of wires 45 transfer signal 110*a*, signals 110*b*, and signal 110*c* from the respective temperature sensor 54 of each electrode element 52 to the second portion 142*a* of the connector 42*a*-1. The distal circuit 40 processes the plurality of signals 110*b* into a DATA signal and transmits the DATA signal along one of four conductors 51, e.g., GND, VCC, DATA, and TTF, of a 4-wire cable 35 as discussed above in more detail.

Figure 10:
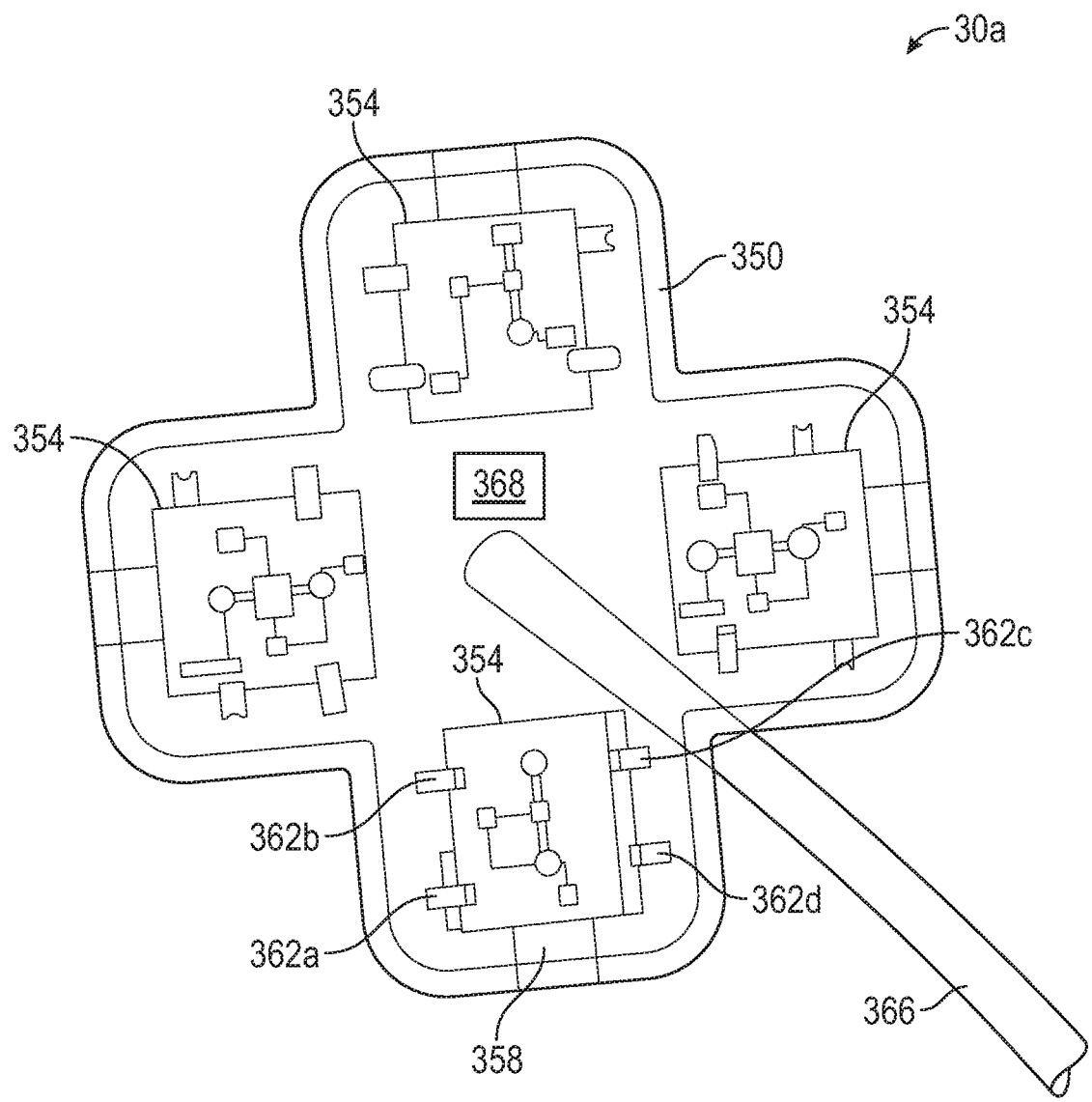
FIG. 10 is a diagram of an exemplary embodiment of a hub constructed in accordance with the present disclosure.

Referring now to FIG. 10, shown therein is a diagram of an exemplary embodiment of a hub 30*a* constructed in accordance with the present disclosure. The hub 30*a* generally comprises a housing 350 supporting a plurality of array connectors 354. Each array connector 354 may be a 4-wire connector, constructed similar to the connector 42*c* or 42*d* as shown in FIGS. 5D and 5E except as discussed below. Each array connector 354 may be positioned within the housing 350. However, in some embodiments, not shown in FIG. 10, one or more array connector 354 is not integrated into the housing 350 but is separate from the housing 350.

As shown in FIG. 10, each array connector 354 of the hub 30*a* includes a port 358 operable to receive a first portion 140, for example, such as a first portion 140*c* or a second portion 142*d*, and may include at least four pins 362*a-d* operable to electrically couple the port 358 to a cable 366. Each of the four pins 362*a-d* may be associated with and couple a VCC signal, GND signal, DATA signal, and a TTField Signal from a respective transducer array 50 to the electric field generator 20.

In one embodiment, each transducer array 50 connected to the hub 30*a* includes the distal circuit 40 at a location between each of the respective electrode elements 52 and the port 358 operable to receive a plug, such as, for example, the first portion 140*a* or the first portion 140*d*. In one embodiment, the plug is electrically coupled to the first distal circuit 40, such as shown in FIG. 8, and to each of the conductors 51 via the 4-wire cable 35. In one embodiment, the plug and the port 358 (e.g., TRRS connector) are a 3.5 mm "audio jack", that is the plug is a TRRS plug and the port 358 is a TRRS socket or port. In this embodiment, the cable 366 is used in place of the cable 25 shown in FIG. 1.

In one embodiment, the cable 366 may include at least 10 wires and may be constructed similar to the cable 25 (if each port 358 uses a common GND conductor 51 and a common VCC conductor 51) and may include up to 16 wires (if each port 358 uses an independent GND conductor 51 and an independent VCC conductor 51). In one embodiment, the cable 366 is a USB-C cable and is connected to the hub 30*a* via a USB-C connection. In one embodiment, each transducer array 50 is connected to the hub 30*a* via a USB-C cable and the port 358 is a USB-C port.

In one embodiment, the housing 350 of the hub 30*a* may further include an attaching member 368. The attaching member 368 may be attached to the housing 350 and allow a user to attach the hub 30*a* to the user. In some embodiments, the attaching member 368 is affixed to any hub 30 herein described. In some embodiments, the attaching member 368 is affixed to the module 60 and/or to the substrate 59 herein described.

In one embodiment, the housing 350 is flexible. In this embodiment, the housing 350 conforms to contours of a surface on which the hub 30*a* is placed. For example, if the hub 30*a* is placed on a patient's body, the housing 350 conforms to the patient's body, or if the hub 30*a* is placed on a particular transducer array 50, the housing 350 conforms to the transducer array 50.

In one embodiment, the attaching member 368 is a clip attaching member. The clip attaching member may allow a user to affix the hub 30*a* to the user, e.g., to the user's clothing by clipping the hub 30*a* to the user's clothing.

In one embodiment, the attaching member 368 is an adhesive attaching member having a tackiness, and may also be referred to as a wearable patch. The adhesive attaching member may allow a user to affix the hub 30*a* to the user, for example to the user's clothing or to the user's skin, by using an adhesive. In one embodiment, such as when the adhesive attaching member is affixed to the patient's skin, the adhesive may be biocompatible for an extended period of time, that is, the adhesive attaching member will adhere, or stick, to the patient's skin and is not likely to cause a reaction with the patient's skin.

In one embodiment, the adhesive attaching member will include the housing 350 that is flexible. In this embodiment, the housing 350 is flexible so as to allow the housing 350 to conform to contours of the patient's body at the location the adhesive attaching member is placed on the patient, e.g., on the patient's skin.

In one embodiment, the attaching member 368 is a hook and loop fastener. In this embodiment, the attaching member 368 may include a hook component and a loop component. One of the hook component and the loop component may be attached to the housing 350 while the other of the hook component and the loop component may be attached to the patient, e.g., by an adhesive such as the adhesive described above. In this manner, the hook component or the loop component attached to the housing 350 can engage the hook component or the loop component attached to the patient. In another embodiment the other of the hook component and the loop component may be attached to the patient's skin, the patient's clothing, a particular electrode array 50, or otherwise attached to the patient at a particular distance from the electrode arrays 50. In one embodiment, a suitable hook and loop fastener is identified by the brand name VELCRO®, manufactured by the Velcro Companies, trademark owned by Velcro IP Holdings LLC.

Figure 11A:
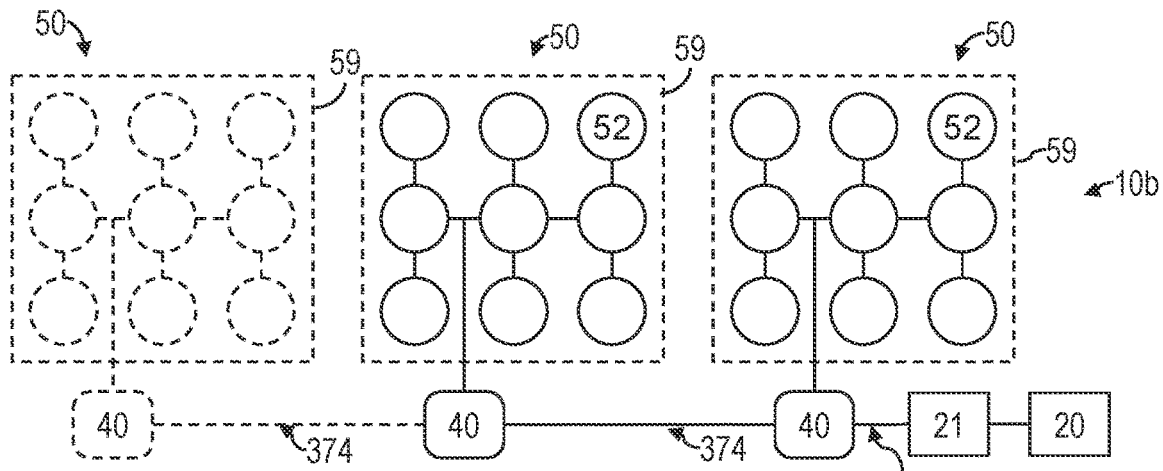
FIG. 11A-C are diagrams of exemplary embodiments of the system of FIG. 6 having varying arrangements of a plurality of the transducer arrays linked together and the distal circuit constructed in accordance with the present disclosure.
Figure 11B:
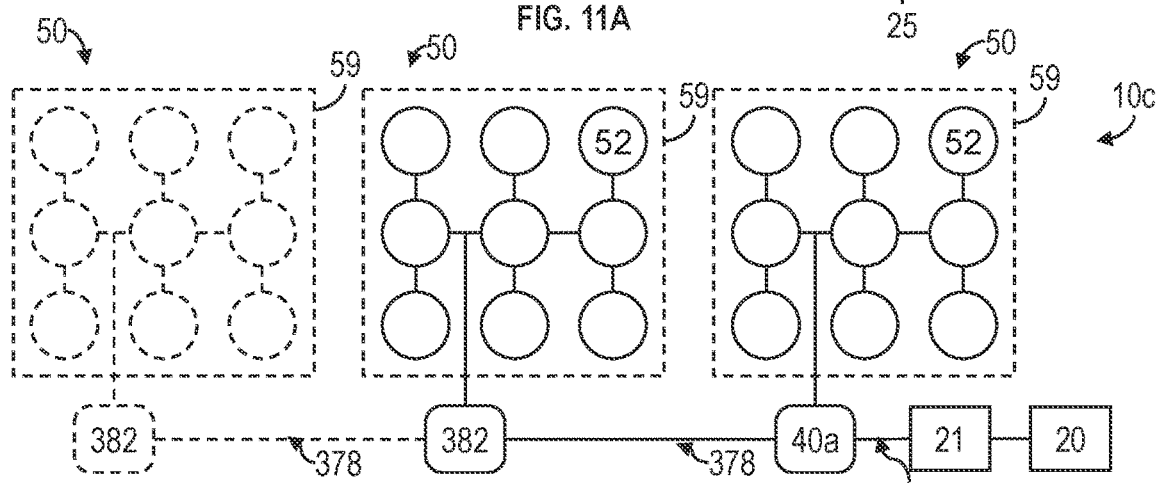
Figure 11C:
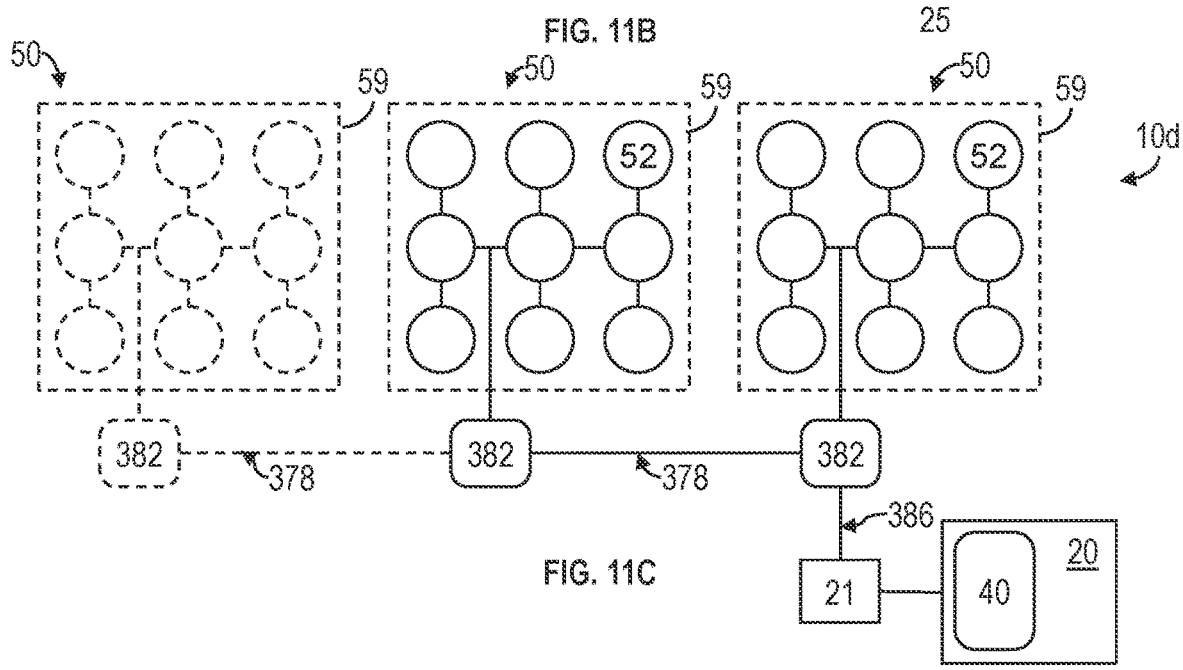

Referring now to FIGS. 11A-11C in combination, shown therein are diagrams of exemplary embodiments of the system 10 having varying arrangements of a plurality of the transducer arrays 50 linked together and the distal circuit 40 constructed in accordance with the present disclosure.

Referring now to FIG. 11A, shown therein is a system 10b having a plurality of transducer arrays 50 "daisy chained" together and constructed in accordance with the present disclosure. Each transducer array 50 is associated with a respective first distal circuit 40 such that, when a first transducer array 50 is connected to a second transducer array 50, signals, such as the VCC signal, GND signal, DATA signal, and TTField Signal, from the first transducer array 50 are passed through the second transducer array 50 to the signal connector 21. The signal connector 21 is in circuit with the electric field generator 20 and passes the signals to the electric field generator 20. In one embodiment, the first distal circuit 40 of the second transducer array 50, and the signal connector 21 do not perform any processing on the signals from the first transducer array 50. Each of the first distal circuit 40 may be a part of a module 60 as described above.

In one embodiment, each first distal circuit 40 implements a standard communication protocol such as 1-wire, SPI, or I2C thereby reducing the number of wires needed for communication between the electric field generator 20 and each distal circuit 40. For example, instead of the UART 86, each distal circuit 40 may be implemented to encode/decode data with a communication protocol. The communication protocol may conform to the requirements of at least one of 1-wire, SPI, or I2C. In one embodiment, by daisy chaining the transducer arrays 50 and implementing a communication protocol such as I2C, the number of wires required in each cable 374 may be reduced to just 5 wires between the electric field generator 20 and each of the first distal circuit 40 associated with each transducer array 50. In one embodiment, the distal circuit 40 may be integrated into either the first side or the second side of a connector attached to the cable 374.

Referring now to FIG. 11B, shown therein is a system 10c constructed similar to the system 10a and the system 10b described above, except the system 10c has a plurality of transducer arrays 50 "daisy chained" together where only one of the transducer arrays 50 has a distal circuit 40a. Each transducer array 50 is associated with a cable 378 such that, when a first transducer array 50 is connected to a second transducer array 50, signals 110a and signals 110b are transmitted from the first transducer array 50 and are passed through the second transducer array 50 at a junction 382. In one embodiment, the distal circuit 40a receives the signals 110a and signals 110b from each of the other transducer arrays 50 chained together and, as described above in more detail, processes the signals 110b into a DATA signal for each of the transducer arrays 50. The distal circuit 40a, in this embodiment, may be a combination of the hub 30 and the distal circuit 40 such that the distal circuit 40a controls operation of each transducer array 50 and transforms the signals 110b into a DATA signal for the electric field generator 20. The cable 25, communicably coupling the electric field generator 20 to the distal circuit 40a (via signal connector 21), may therefore include eight (8) wires as detailed above and shown in FIG. 2. Each of the junction 382 may be a part of a module 60 as described above. In one embodiment, the distal circuit 40 may be integrated into either the first side or the second side of a connector attached to the junction 382.

Referring now to FIG. 11C, shown therein is a system 10d constructed similar to the system 10a, the system 10b, and the system 10c described above, except the system 10d has a plurality of transducer arrays 50 "daisy chained" together where none of the transducer arrays 50 have a distal circuit 40. Each transducer array 50 is associated with a cable 378 such that, when a first transducer array 50 is connected to a second transducer array 50, signals 110 are transmitted from the first transducer array 50 and are passed through the second transducer array 50 at a junction 382. In one embodiment, all signals 110a and all signals 110b from each of the transducer arrays 50 chained together is combined into a single cable 386 such that the cable 386 includes a set of wires associated with each of the transducer arrays 50 resulting in at least 10 wires per transducer array 50 if each transducer array 50 uses an independent ground signal 110c and ACC signal 110a or at least 8 wires per transducer array 50, plus a ground wire and an ACC wire, if each transducer array 50 uses a common ground signal 110c and a common ACC signal 110a. In this embodiment, the distal circuit 40 is integrated with the electric field generator 20 (as shown in FIG. 11C), or in some embodiments, the distal circuit 40 is integrated into the connector 21. Each of the junction 382 may be a part of a module 60 as described above. In one embodiment, the distal circuit 40 may be integrated into either the first side or the second side of a connector attached to the junction 382.

Figure 12A:
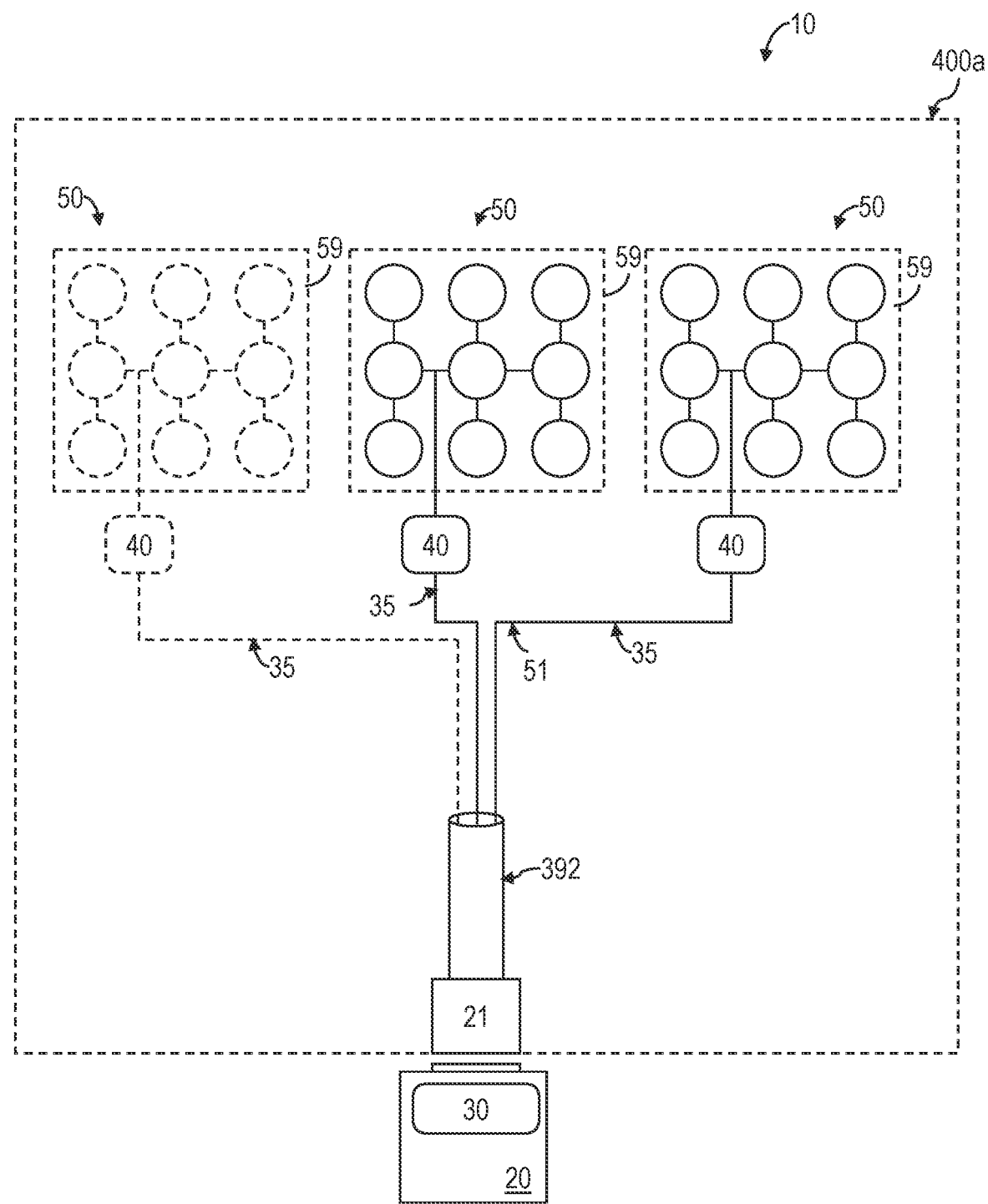
FIG. 12A-D are diagrams of exemplary embodiments of the system having a pre-strung array kit constructed in accordance with the present invention.
Figure 12B:
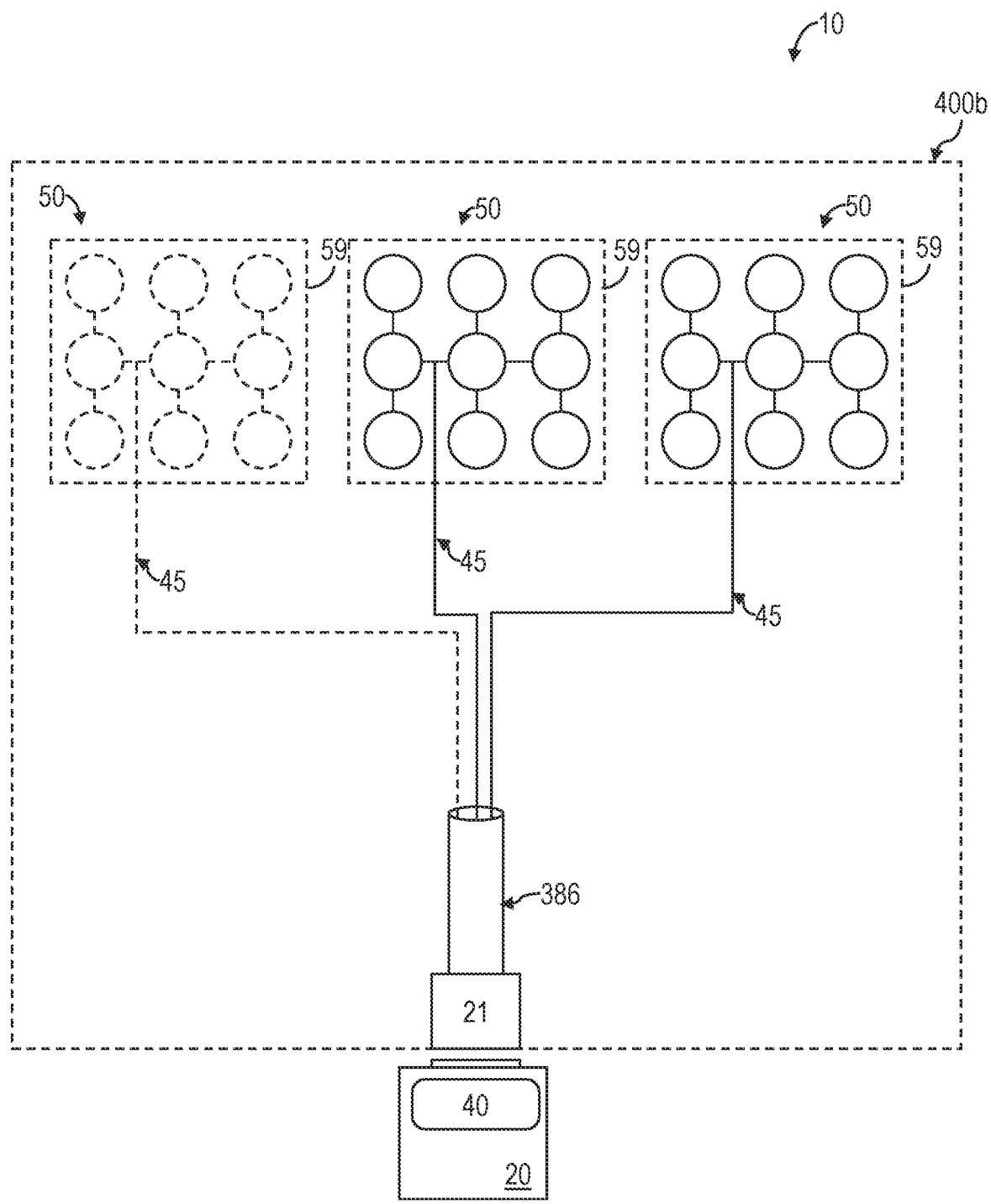
Figure 12C:
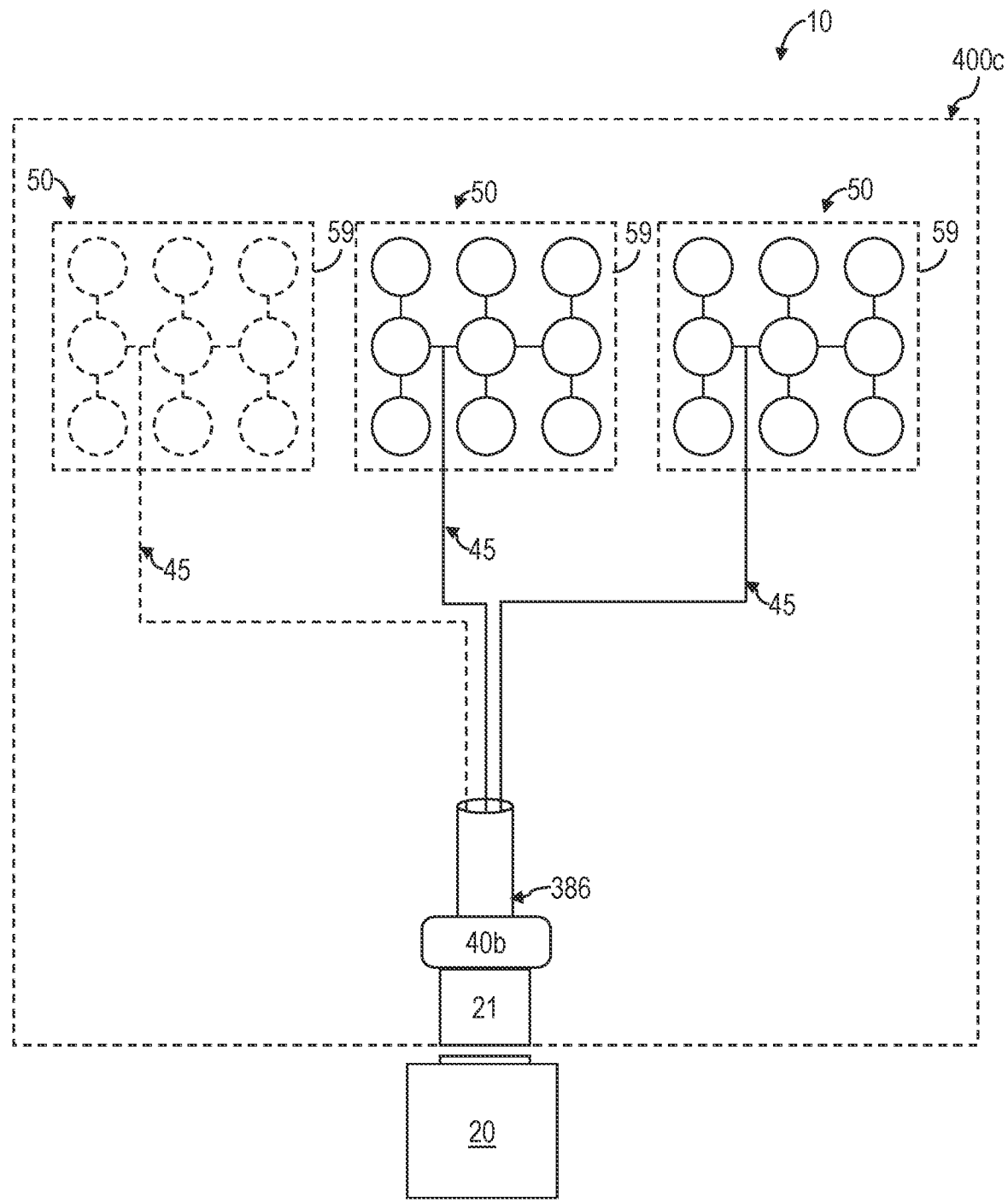

Referring now to FIGS. 12A-12C in combination, shown therein are diagrams of exemplary embodiments of the system 10 having a pre-strung array kit 400 constructed in accordance with the present invention. Each pre-strung array kit 400 includes a plurality of transducer arrays 50, communicably coupled to a signal connector 21.

Referring to FIG. 12A, shown therein is a pre-strung array kit 400a having a plurality of transducer arrays 50, with each transducer array 50 communicably coupled to a particular distal circuit 40. As described in more detail above, each distal circuit 40 is connected to conductors 51 of a particular cable 35. As shown in FIG. 12A, all of the conductors 51 of the cables 35 may be combined into a cable 392. The cable 392 includes the signal connector 21 operable to communicably couple the cable 392 to the electric field generator 20. In this embodiment, the electric field generator 20 may include circuitry similar in function to that of the hub 30. For example, each distal circuit 40 may convert the temperature readings into a digital reading and forward that digital reading and/or send the temperature readings to the electric field generator 20. Each of the distal circuits 40 may be a part of a module 60 as described above.

In one embodiment, the pre-strung array kit 400a includes four transducer arrays 50 wherein each transducer array 50 is communicably coupled to a particular distal circuit 40 as described above.

Referring to FIG. 12B, shown therein is an exemplary embodiment of the system 10 including a pre-strung array kit 400b having a plurality of transducer arrays 50, each transducer array 50 having a plurality of wiring 45. The wiring 45 from each of the transducer arrays 50 is combined into a cable 386. The cable 386 includes the signal connector 21 operable to communicably couple the cable 386 to the electric field generator 20. In this embodiment, the electric field generator 20 may include circuitry similar in function to that of the distal circuit 40 and/or the hub 30. The electric field generator 20 may include any analog-digital circuitry, such as digital converter 83, and directly read the temperature sensor 54 for each respective electrode elements 52 of each respective transducer array 50. Additionally, the electric field generator 20 may directly control the TTField Signal for each of the respective transducer array 50.

In one embodiment, the pre-strung array kit 400b includes four transducer arrays 50 wherein each transducer array 50 includes wiring 45 that is combined into the cable 386 as described above.

Referring to FIG. 12C, shown therein is a pre-strung array kit 400c having a plurality of transducer arrays 50 with each transducer array 50 having a plurality of wiring 45. The wiring 45 from each of the transducer arrays 50 is combined into the cable 386. The cable 386 is communicably coupled to the distal circuit 40b which further is coupled to signal connector 21. The distal circuit 40b may be included on a module 60 and may include a clip 368 as described above. Similar to the functioning of the distal circuit 40a described above, the distal circuit 40b receives the signals 110a and signals 110b from each of the transducer arrays 50 via the wiring 45 combined in the cable 386 and, as described above in more detail, processes the signals 110b into a DATA signal for each of the transducer arrays 50 before transmitting the DATA signal to the electric field generator 20 via the signal connector 21. The distal circuit 40b may include any analog-digital circuitry, such as digital converter 83, and directly read the temperature sensor 54 for each respective electrode elements 52 of each respective transducer array 50 and may include circuitry such as circuitry of the hub 30 shown in FIG. 2.

In one embodiment, the pre-strung array kit 400c includes four transducer arrays 50 wherein each transducer array 50 includes wiring 45 that is combined into the cable 386 and coupled to the distal circuit 40b as described above.

In one embodiment, the distal circuit 40b is integrated with the signal connector 21. The signal connector 21 may then be electrically coupled to the electric field generator 20. In some embodiments, the signal connector 21 is slidably coupled to the electric field generator 20. In some embodiments, the signal connector 21 may be removably attached to the electric field generator 20. In one embodiment, the signal connector 21 includes one or more indicator electrical connector, constructed similar to the indicator electrical connector 202 described above. In some embodiments, the signal connector 21 is constructed similar to one of the connector 42c, the connector 42d, the connector 42e, and/or the connector 42f, with the exception that the signal connector 21 may have more or fewer electrical connectors 200 as determined by a number of conductors required for a particular embodiment.

In one embodiment, the pre-strung array kit 400c includes a cable between the distal circuit 40b and the signal connector 21. In some embodiments, the cable may be a spiral cable such as spiral cable 25' shown in FIG. 13 and discussed below in more detail. As described above, the distal circuit 40b may also include the attaching member 368 to enable the user to affix the distal circuit 40b to their clothing, for example.

In one embodiment, the pre-strung array kit 400c includes a second cable between the signal connector 21 and the electric field generator 20. In this embodiment, the second cable may be a spiral cable, such as spiral cable 25' discussed below. The second cable may include a first connector operable to receive the signal connector 21 at a first end and a second connector constructed similar to the signal connector 21 at a second end. In this way, the second cable may be used to increase a distance between the electric field generator 20 and the pre-strung array kit 400c. When the second cable is no longer desired, the signal connector 21 may be disconnected from the first connector, the second connector may be disconnected from the electric field generator 20, and the signal connector 21 may be coupled to the electric field generator 20 in place of the second connector.

Figure 12D:
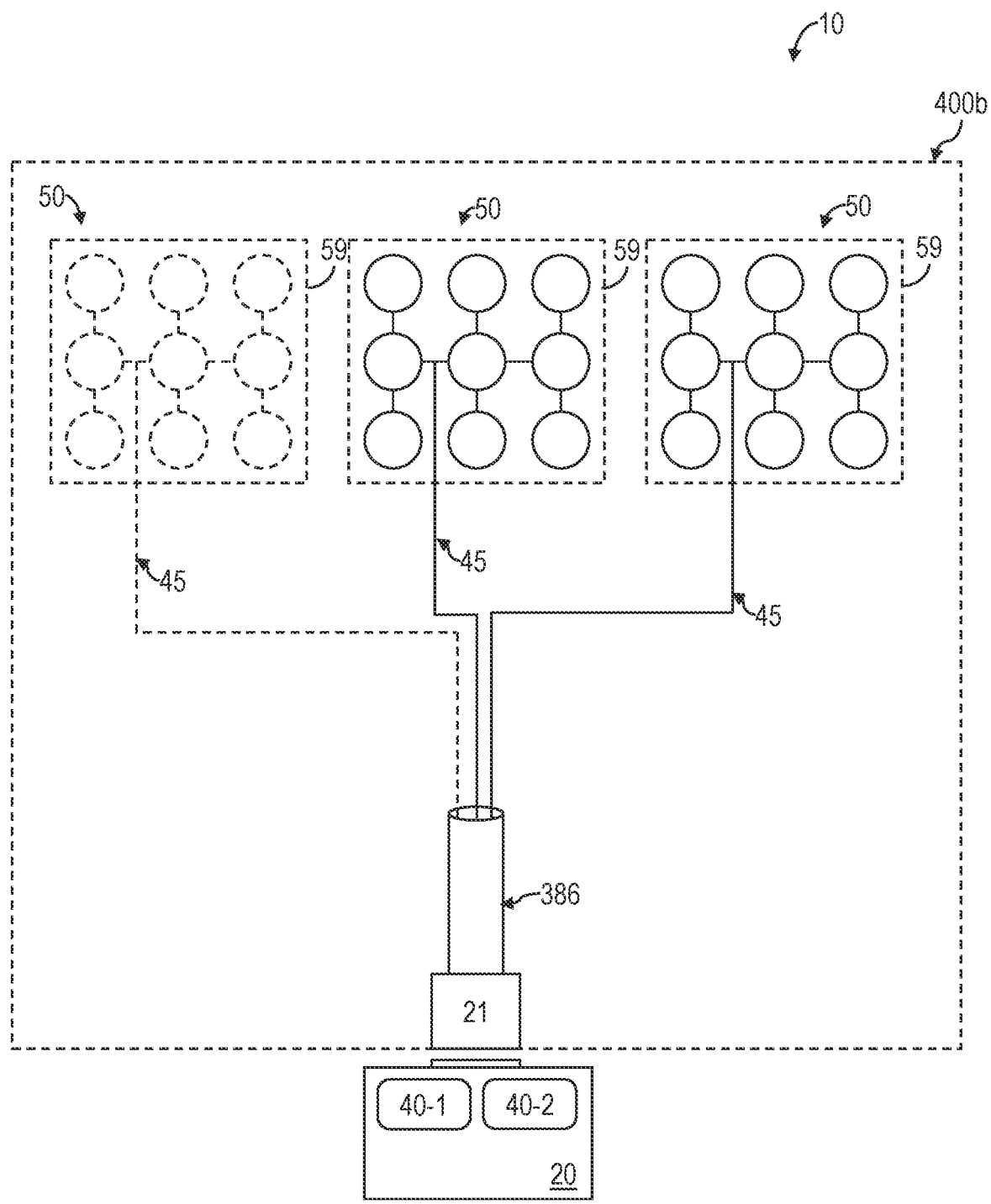

Referring now to FIG. 12D, shown therein is an exemplary embodiment of the system 10 of FIG. 12B with the exception that the electric field generator 20 includes more than one distal circuit 40. The system 10 of FIG. 12D generally includes a pre-strung array kit 400b having a plurality of transducer arrays 50, each transducer array 50 having a plurality of wiring 45. The wiring 45 from each of the transducer arrays 50 is combined into a cable 386. The cable 386 includes the signal connector 21 operable to communicably couple the cable 386 to the electric field generator 20. In this embodiment, the electric field generator 20 may include more than one circuitry similar in function to that of the distal circuit 40 and/or the hub 30. For example, the electric field generator 20 may include a first distal circuit 40-1 and a second distal circuit 40-2. The electric field generator 20 may also include any analog-digital circuitry, such as digital converter 83, and directly read the temperature sensor 54 for each respective electrode elements 52 of each respective transducer array 50. Additionally, the electric field generator 20 may directly control the TTField Signal for each respective transducer array 50. In one embodiment, the electric field generator 20 may include more than two distal circuits 40, e.g., the first distal circuit 40-1 and the second distal circuit 40-2. In one embodiment, the electric field generator 20 may include a number of distal circuits 40 equal to the number of transducer arrays 50. In one embodiment, the electric field generator 20 may include up to a number of distal circuits 40 needed to communicate to a number of transducer arrays 50 required to administer a therapeutically effective TTField.

Figure 13:
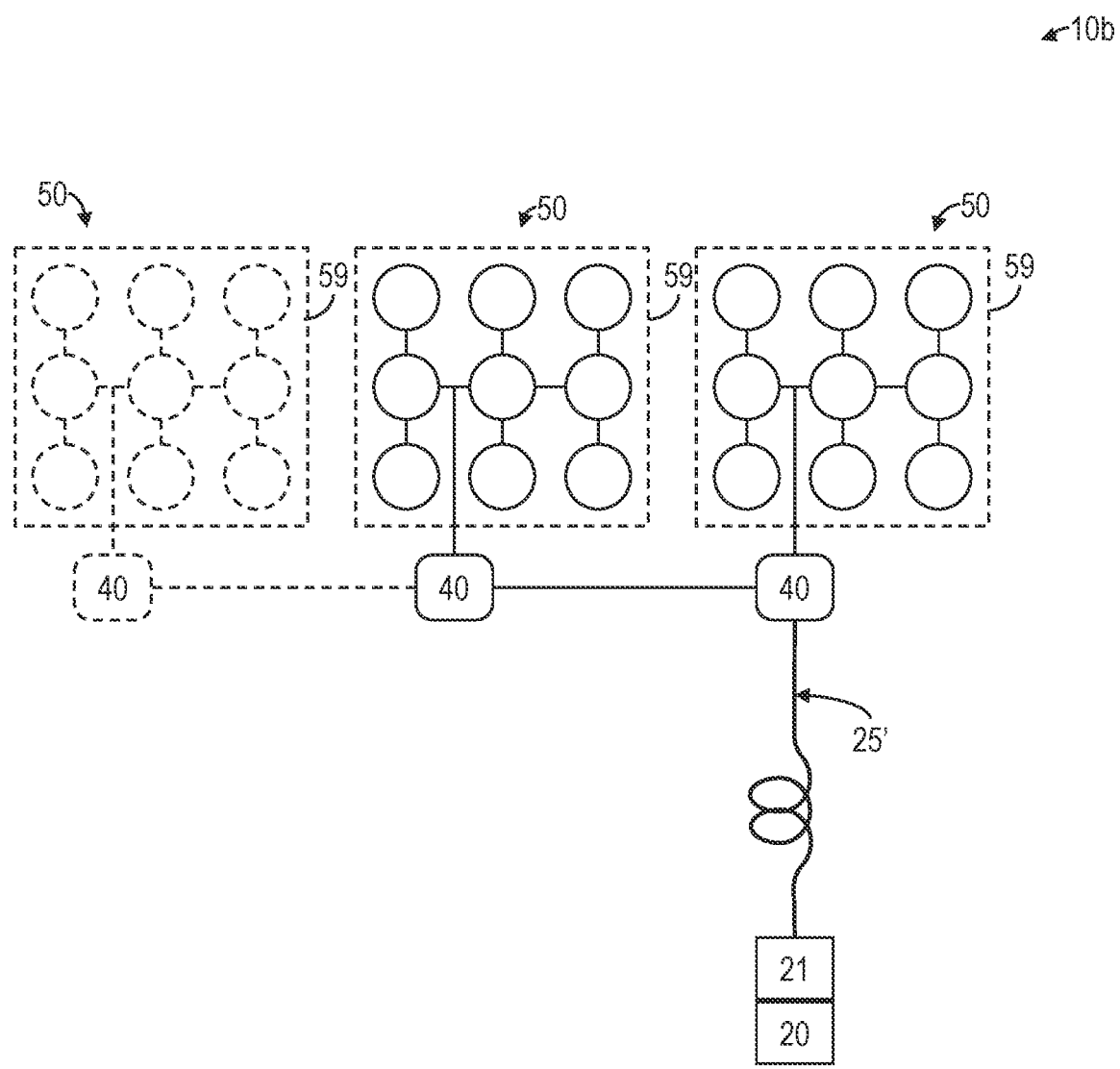
FIG. 13 is a diagram of an exemplary embodiment of the system having a spiral cable and constructed in accordance with the present disclosure.

Referring now to FIG. 13, shown therein is a diagram of an exemplary embodiment of the system 10b constructed in accordance with the present disclosure with the exception that the cable 25 is a cable 25'. The cable 25' is similar in form and function to the cable 25, with the exception that the cable 25' is a spiral cable 25. By utilizing the cable 25', any force such as at the signal connector 21 caused by movement of the transducer arrays 50 when using the cable 25 is absorbed by the cable 25' when using the cable 25', thereby reducing the likelihood of disconnecting the cable 25' from the electric field generator 20. In one embodiment, the full length of the cable 25' has a spiral form, however, in another embodiment, the full length of the cable 25' does not have a spiral form.

While the cable 25' is shown as being a spiral cable, other cables or wires in any of the systems 10 described above may be spiral cables. For example, one or more of the cable 25, the cable 35, the cable 366, the cable 374, the cable 378, the cable 386, and the cable 392 may be formed to have one or more spiral, either across the full length of the respective cable, or across a less than full length of the respective cable.

NON-LIMITING ILLUSTRATIVE EMBODIMENTS OF THE INVENTIVE CONCEPT(S)

The following is a number list of non-limiting illustrative embodiments of the inventive concept disclosed herein:

Illustrative Embodiment 1. An apparatus for imposing electric fields through a target region in a body of a patient, the apparatus comprising:
- at least one transducer array having a plurality of electrode elements configured for placement on the body of the patient, the electrode elements configured to provide TTFields; and
- a connector electrically connected to the at least one transducer array, wherein the connector has at least one associated monitoring circuit configured to provide feedback related to a status of the connector.

Illustrative Embodiment 2. The apparatus of Illustrative Embodiment 1, wherein the connector has a plurality of pins or socket connectors in electrical communication with the transducer array, and wherein at least one of the pins or socket connectors is an indicator electrical connector.

Illustrative Embodiment 3. The apparatus of Illustrative Embodiment 2, wherein the connector further comprises:
- a first portion, wherein the indicator electrical connector is an indicator pin integrated into the first portion of the connector; and
- a second portion including an indicator socket connector associated with the indicator pin, the indicator socket connector integrated into the second portion of the connector.

Illustrative Embodiment 4. The apparatus of Illustrative Embodiment 3, wherein the plurality of pins is integrated into the first portion of the connector and wherein the second portion of the connector further includes a plurality of socket connectors wherein each socket connector is operable to receive a particular one of the plurality of pins integrated into the first portion of the connector.

Illustrative Embodiment 5. The apparatus of Illustrative Embodiment 3, wherein a first length of at least one of the plurality of pins is greater than a second length of the at least one indicator pin.

Illustrative Embodiment 6. The apparatus of Illustrative Embodiment 4, wherein a first depth of the plurality of socket connectors is greater than a second depth of the indicator socket connector.

Illustrative Embodiment 7. The apparatus of Illustrative Embodiment 6, wherein the connector further includes a first end and a second end with the indicator pin positioned at the first end of the connector.

Illustrative Embodiment 8. The apparatus of Illustrative Embodiment 3, further comprising at least one resistor in electrical communication with the indicator socket connector, wherein feedback related to the status of the connector includes voltage changes at the at least one resistor.

Illustrative Embodiment 9. The apparatus of Illustrative Embodiment 3, wherein the connector further includes at least two indicator pins, a first end, and a second end, wherein at least one indicator pin is positioned at the first end of the connector and at least one indicator pin is positioned at the second end of the connector.

Illustrative Embodiment 10. The apparatus of Illustrative Embodiment 9, further comprising a conductive line positioned between at least two indicator socket connectors forming a monitoring circuit.

Illustrative Embodiment 11. The apparatus of Illustrative Embodiment 10, wherein a controller is configured to determine the status of the connector via the monitoring circuit.

Illustrative Embodiment 12. The apparatus of Illustrative Embodiment 11, wherein the controller determines the status of the connector by monitoring changes to current within the monitoring circuit or by monitoring changes to voltage within the monitoring circuit.

Illustrative Embodiment 13. The apparatus of Illustrative Embodiment 1, wherein the at least one monitoring circuit is configured to generate a signal indicative of the status of the connector, and further comprising an indicator system configured to receive the signal and provide at least one of visual, auditory or haptic feedback to a user on the status of the connector.

Illustrative Embodiment 14. The apparatus of Illustrative Embodiment 1, further comprising an electric field generator, wherein the connector includes a first portion configured to be connected to a second portion, and wherein the status of the connector is "disconnection" or "partial disconnection" of the first portion from the second portion, and wherein the monitoring circuit is configured to generate a signal indicative of the status of the connector of "disconnection" or "partial disconnection" of the first portion and the second portion, and further wherein the electric field generator receives a signal that indicates the status of the connector of "disconnection" or "partial disconnection" of the first portion and the second portion and powers down the electric field generator.

Illustrative Embodiment 15. A method for monitoring an apparatus for imposing electric fields through a target region in a body of a patient, the method comprising:
- electrically connecting a connector to the at least one transducer array, wherein the at least one transducer array has a plurality of electrode elements configured for placement on the body of the patient, the electrode elements configured to provide TTFields;
- circulating current through at least one indicator pin integrated into a first portion of the connector, and an associated indicator socket connector integrated into a second portion of the connector;
- monitoring data from the circulating current;
- determining status of the connector based on the monitored data; and,
- providing a predetermined action based on the status of the connector.

Illustrative Embodiment 16. The method of Illustrative Embodiment 15, wherein the predetermined action is providing at least one of visual indicator, auditory indicator, or haptic indicator of the status of the connector to a user.

Illustrative Embodiment 17. The method of Illustrative Embodiment 15, wherein the connector is configured to be connected to an electric field generator, and wherein the status of the connector is "disconnection" or "partial disconnection" of the at least one indicator pin from an associated indicator socket connector, and wherein the predetermined action is powering down the electric field generator.

Illustrative Embodiment 18. A system comprising:
a plurality of transducer arrays each having substrate supporting a plurality of electrode elements configured for placement on a body of a patient, the electrode elements configured to provide TTFields and at least one electrode element associated with a temperature sensor; each transducer array electrically connected to a first side of a connector, and each transducer array comprising a distal circuit electrically coupled to each of the plurality of electrode elements of the transducer array and operable to receive a temperature signal from each of the associated temperature sensors and operable to output a DATA signal and to receive a TTField Signal, the distal circuit being either supported by the substrate, or integrated into the first side of the connector, or both, or positioned in a circuit between the transducer array and the connector, the connector further comprising a plurality of pins or socket connectors in electrical communication with the transducer array; and, at least one monitoring circuit configured to provide feedback related to a status of the connector;
a hub electrically coupled to each of the plurality of transducer arrays; and
an electric field generator electrically coupled to the hub and operable to receive one or more DATA signal and output one or more TTField Signal.

Illustrative Embodiment 19. The system of Illustrative Embodiment 18, wherein the connector further comprises a first end and a second end; and wherein the monitoring circuit is coupled to at least one indicator electrical connector comprising a first indicator pin and a second indicator pin, the first indicator pin positioned at the first end of the connector and the second indicator pin positioned at the second end of the connector; the connector further comprising a conductive line positioned between at least two indicator socket connectors forming the monitoring circuit configured to determine the status of the connector.

Illustrative Embodiment 20 The system of Illustrative Embodiment 18, wherein the monitoring circuit generates a signal indicative of the status of the connector of "disconnection" or "partial disconnection" of the first portion and the second portion, and wherein the electric field generator receives a signal that indicates the status of the connector of "disconnection" or "partial disconnection" of the first portion and the second portion and powers down the electric field generator.

Illustrative Embodiment 21. A connector for use in a TTField system, comprising:
a first portion having:
a plurality of pins integrated into the first portion and configured to be electrically connected to an array of transducers; and,
at least one indicator pin integrated into the first portion, the at least one indicator pin having a first length less than a second length of at least one of the plurality of pins.

Illustrative Embodiment 22. A method, comprising:
circulating current through at least one indicator pin integrated into a first portion of a connector, and an associated indicator socket connector integrated into a second portion of a connector;
monitoring data from the circulating current;
determining status of the connector based on the monitored data; and,
providing at least one visual indicator of the status of the connector to a user.

Illustrative Embodiment 23. A connector for use in a TTField system, comprising:
a first portion having:
a plurality of electrical connectors integrated into the first portion and configured to be electrically connected to an array of transducers; and,
at least two indicator electrical connectors integrated into the first portion; and
a conductor electrically connecting the two indicator electrical connectors.

Illustrative Embodiment 24. An apparatus for use in a TTF field system, comprising:
at least one transducer array having a plurality of electrode elements configured for placement on a body of a patient, the electrode elements configured to provide TTFields;
a connector electrically connected to the at least one transducer array, the connector having a first portion comprising:
a plurality of electrical connectors in electrical communication with the transducer array; and,
at least one indicator electrical connector electrically isolated from the transducer array, and configured to provide feedback related to a status of the connector.

Illustrative Embodiment 25. An apparatus for imposing electric fields through a target region in a body of a patient, the apparatus comprising:
at least one transducer array having a plurality of electrode elements configured for placement on the body of the patient and at least one temperature sensor, the electrode elements configured to provide TTFields;
a distal circuit electrically coupled to the at least one transducer array and operable to receive a temperature signal from the at least one temperature sensor; and
a connector electrically connected to the distal circuit, the distal circuit positioned in a circuit between the transducer array and the connector.

Illustrative Embodiment 26. The apparatus of illustrative embodiment 25, wherein at least one electrode element is associated with a temperature sensor.

Illustrative Embodiment 27. The apparatus of illustrative embodiment 25, wherein the distal circuit is integrated into a first side of the connector.

Illustrative Embodiment 28. The apparatus of illustrative embodiment 27, wherein the connector comprises at least four pins or socket connectors in electrical communication with the transducer array.

Illustrative Embodiment 29. The apparatus of illustrative embodiment 25, wherein the distal circuit is integrated into each of the at least one transducer array.

Illustrative Embodiment 30. The apparatus of illustrative embodiment 25, wherein the at least one transducer array has a substrate, and wherein the distal circuit is supported by the substrate.

Illustrative Embodiment 31. The apparatus of illustrative embodiment 25, wherein the at least one transducer array has a substrate, and the distal circuit is not supported by the substrate.

Illustrative Embodiment 32. The apparatus of illustrative embodiment 25, wherein the distal circuit comprises at least two of: analog-digital converter, analog multiplexer, digital multiplexer, controller, transceiver.

Illustrative Embodiment 33. A system comprising:
a plurality of transducer arrays each having substrate supporting a plurality of electrode elements configured for placement on the body of a patient, the electrode elements configured to provide TTFields and at least one electrode element associated with a temperature sensor; each transducer array electrically connected to a first side of a connector, and each transducer array comprising a distal circuit electrically coupled to each of the plurality of electrode elements of the transducer array and operable to receive a temperature signal from each of the associated temperature sensors and operable to output a DATA signal and to receive a TTField Signal, the distal circuit being either supported by the substrate, or integrated into the first side of the connector, or both, or positioned in a circuit between the transducer array and the connector;

a hub electrically coupled to each of the plurality of transducer arrays; and an electric field generator electrically coupled to the hub and operable to receive one or more DATA signal and output one or more TTField Signal.

Illustrative Embodiment 34. The system of illustrative embodiment 33, wherein each of the plurality of transducer arrays is electrically coupled to a cable having a second side of the connector and electrically coupled to the hub.

Illustrative Embodiment 35. The system of illustrative embodiment 34, wherein the cable is a spiral cable.

Illustrative Embodiment 36. The system of illustrative embodiment 34, wherein the cable comprises 4 conductors.

Illustrative Embodiment 37. The system of illustrative embodiment 34, wherein the cable is electrically coupled to the hub via a TRRS connector.

Illustrative Embodiment 38. The system of illustrative embodiment 33, further comprising a cable electrically coupled to the hub and electrically coupled to the electric field generator.

Illustrative Embodiment 39. The system of illustrative embodiment 38, wherein the cable is a spiral cable.

Illustrative Embodiment 40. The system of illustrative embodiment 33, wherein the hub further includes an attaching member selected from a clip, an adhesive, and a hook component or loop component of a hook and loop fastener.

Illustrative Embodiment 41. The system of illustrative embodiment 40, wherein the hook and loop fastener is a Velcro fastener.

Illustrative Embodiment 42. A system comprising:

a plurality of transducer arrays each having a plurality of electrode elements configured for placement on the body of a patient and at least one temperature sensor, the electrode elements configured to provide TTFields; each transducer array having a first side of a connector;

a hub comprising a distal circuit electrically coupled to each of the plurality of transducer arrays and operable to receive a temperature signal from the at least one temperature sensor and operable to output a DATA signal and to receive a TTField Signal for each of the plurality of transducer arrays; and an electric field generator electrically coupled to the hub and operable to receive one or more DATA signal and output one or more TTField Signal.

Illustrative Embodiment 43. The system of illustrative embodiment 42, wherein at least one electrode element is associated with a temperature sensor.

Illustrative Embodiment 44. A system comprising:

a plurality of transducer arrays each comprising a substrate supporting a plurality of electrode elements configured for placement on the body of a patient and at least one temperature sensor, the electrode elements configured to provide TTFields;

at least one distal circuit operable to receive a temperature signal from the at least one temperature sensor of the plurality of transducer arrays and operable to output a DATA signal and to receive a TTField Signal; and an electric field generator electrically coupled to the at least one distal circuit and operable to receive one or more DATA signal and output one or more TTField Signal.

Illustrative Embodiment 45. The system of illustrative embodiment 44, wherein at least one electrode element is associated with a temperature sensor.

Illustrative Embodiment 46. The system of illustrative embodiment 44 wherein the at least one distal circuit is integrated into each of the transducer arrays.

Illustrative Embodiment 47. The system of illustrative embodiment 44 wherein the at least one distal circuit is integrated with the electric field generator.

Illustrative Embodiment 48. The system of illustrative embodiment 44 wherein the at least one distal circuit includes a distal circuit associated with each transducer array and the electric field generator is electrically coupled to each distal circuit.

Illustrative Embodiment 49. The system of illustrative embodiment 48 wherein the plurality of transducer arrays are linked together in a chain and each transducer array has a distal circuit associated with it.

Illustrative Embodiment 50. The system of illustrative embodiment 44 wherein the plurality of transducer arrays consists of n transducer arrays linked together in a chain and there are fewer than n distal circuits present.

Illustrative Embodiment 51. The system of illustrative embodiment 44 wherein the at least one distal circuit is located on a wearable patch which, optionally, may be adhered or affixed to the body of the patient.

Illustrative Embodiment 52. The system of illustrative embodiment 44 wherein the at least one distal circuit is located on a patch adhered or affixed to the substrate.

Illustrative Embodiment 53. The system of illustrative embodiment 44 further comprising a hub electrically connected to each of the plurality of transducer arrays and which hub comprises one of the at least one distal circuit.

Illustrative Embodiment 54. The system of illustrative embodiment 44 wherein the system comprises multiple transducer arrays, each of which has a distal circuit operable to receive a temperature signal from each of the associated temperature sensors of the electrode elements for each transducer array, and wherein each distal circuit is operable to receive DATA signals and output TTField Signals.

Illustrative Embodiment 55. A system comprising:

a first transducer array comprising a first substrate supporting a plurality of first electrode elements configured for placement on the body of a patient and at least one first temperature sensor, the first electrode elements configured to provide TTFields;

a junction electrically coupled to the first transducer array and operable to receive a first temperature signal from the at least one first temperature sensor of the first transducer array and operable to output the first temperature signal, and to receive a first TTField signal; and a second transducer array comprising a second substrate supporting a plurality of second electrode elements configured for placement on the body of the patient and at least one second temperature sensor, the second electrode elements configured to provide TTFields;

a distal circuit operable to receive the first temperature signal from the at least one first temperature sensor of the first transducer array from the junction and to receive a second temperature signal from the at least one second temperature sensor of the second transducer array and operable to output a first DATA signal and a second DATA signal and to receive a first TTField signal and a second TTField signal, wherein the distal circuit communicates with the junction; and an electric field generator electrically coupled to the distal circuit and operable to receive the first DATA signal and the second DATA signal and output the first TTField signal and the second TTField signal.

Illustrative Embodiment 56. The system of illustrative embodiment 55, wherein at least one first electrode element and at least one second electrode element is associated with a temperature sensor.

Illustrative Embodiment 57. A system comprising:
a first transducer array comprising a first substrate supporting a plurality of first electrode elements configured for placement on the body of a patient and at least one first temperature sensor, the first electrode elements configured to provide TTFields;
a first distal circuit operable to receive a first temperature signal from the at least one first temperature sensor of the first transducer array and operable to output a first DATA signal and to receive a first TTField Signal;
a second transducer array comprising a second substrate supporting a plurality of second electrode elements configured for placement on the body of the patient and at least one second temperature sensor, the second electrode elements configured to provide TTFields;
a second distal circuit operable to receive a second temperature signal from the at least one second temperature sensor of the second transducer array and operable to output a second DATA signal and to receive a second TTField Signal;
a cable comprising a first set of wires electrically coupled to the first transducer array and a second set of wires electrically coupled to the second transducer array; and
an electric field generator electrically coupled to the cable and operable to receive the first and second DATA signal and output the first TTField Signal and the second TTField Signal.

Illustrative Embodiment 58. The system of illustrative embodiment 57, wherein at least one first electrode element and at least one second electrode element is associated with a temperature sensor.

Illustrative Embodiment 59. A system comprising:
a first transducer array comprising a first substrate supporting a plurality of first electrode elements configured for placement on the body of a patient and at least one first temperature sensor, the first electrode elements configured to provide TTFields;
a second transducer array comprising a second substrate supporting a plurality of second electrode elements configured for placement on the body of the patient and at least one second temperature sensor, the second electrode elements configured to provide TTFields;
a distal circuit operable to receive a first temperature signal from the at least one first temperature sensor of the first transducer array and a second temperature signal from the at least one second temperature sensor of the second transducer array and operable to output a DATA signal and to receive a TTField Signal;
a cable comprising a first set of wires electrically coupled to the first transducer array and a second set of wires electrically coupled to the second transducer array; and an electric field generator electrically coupled to the cable and operable to receive the first and second DATA signal and output the first TTField Signal and the second TTField Signal.

Illustrative Embodiment 60. The system of illustrative embodiment 59, wherein at least one first electrode element and at least one second electrode element is associated with a temperature sensor.

Illustrative Embodiment 61. A system comprising:
a plurality of transducer arrays, each transducer array having a substrate supporting a plurality of electrode elements configured for placement on the body of a patient and at least one temperature sensor, the electrode elements configured to provide TTFields; each transducer array having a first side of a connector, and each transducer array comprising a distal circuit electrically coupled to the transducer array and operable to receive a temperature signal from the at least one temperature sensor and the distal circuit being operable to at least output a DATA signal and to receive a TTField Signal via a cable, the distal circuit being either supported by the substrate, or integrated into the first side of the connector, or both, the first side of the connector being a TRRS plug;
the cable having four conductors, each conductor having a first end electrically coupled to the distal circuit and a second end electrically coupled to the TRRS plug;
a hub comprising a plurality of TRRS sockets configured to receive the TRRS plug and operable to electrically couple each of the plurality of transducer arrays to the hub; and
an electric field generator electrically coupled to the hub and operable to receive one or more DATA signal and output one or more TTField Signal.

Illustrative Embodiment 62. The system of illustrative embodiment 61, wherein at least one electrode element is associated with a temperature sensor.

Illustrative Embodiment 63. A system comprising:
a plurality of transducer arrays each having substrate supporting a plurality of electrode elements configured for placement on the body of a patient, the electrode elements configured to provide TTFields and at least one electrode element associated with a temperature sensor; each transducer array electrically connected to a first side of a connector, and each transducer array comprising a distal circuit electrically coupled to each of the plurality of electrode elements of the transducer array and operable to receive a temperature signal from each of the associated temperature sensors and operable to output a DATA signal and to receive a TTField Signal, the distal circuit being either supported by the substrate, or integrated into the first side of the connector, or both, the connector further comprising a plurality of pins or socket connectors in electrical communication with the transducer array; and, at least one indicator electrical connector configured to provide feedback related to a status of the connector;
a hub electrically coupled to each of the plurality of transducer arrays; and
an electric field generator electrically coupled to the hub and operable to receive one or more DATA signal and output one or more TTField Signal.

Illustrative Embodiment 64. The system of illustrative embodiment 63, wherein the connector further comprises a first end and a second end; wherein the at least one indicator electrical connector comprises a first indicator pin and a second indicator pin, the first indicator pin positioned at the first end of the connector and the second indicator pin positioned at the second end of the connector; the connector further comprising a conductive line positioned between at least two indicator socket connectors forming a monitoring circuit configured to determine the status of the connector.

Illustrative Embodiment 65. The system of illustrative embodiment 64, further comprising an indicator system operable to provide at least one of visual, haptic, or auditory feedback to a user based at least in part on the status of the connector, and, optionally, to provide at least one associative action to continue use of the connector, or to power down the electric field generator.

Illustrative Embodiment 66. The system of illustrative embodiment 63, wherein the hub is one of disposed between each of the plurality of transducer arrays and the connector or disposed between the connector and the electric field generator.

Illustrative Embodiment 67. A method comprising:
monitoring at least one of a relative location and orientation of a first portion of a connector relative to a second portion of the connector;
determining a status of the connector based on the at least one relative location and orientation; and,
providing a predetermined action based on the status of the connector.

While the present invention has been disclosed with reference to certain embodiments and illustrations, numerous modifications, alterations, and changes to the described embodiments or illustrations are possible without departing from the spirit and scope of the present invention, as defined in the appended claims. Accordingly, it is intended that the present invention not be limited to the described embodiments and illustrations, but that it has the full scope defined by the language of the following claims, and equivalents thereof.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features and steps are recited in the claims and/or disclosed in the specification, these combinations are not intended to limit the disclosure. In fact, many of these features and steps may be combined in ways not specifically recited in the claims and/or disclosed in the specification. Although each dependent claim listed below may directly depend on only one other claim, the disclosure includes each dependent claim in combination with every other claim in the claim set.

Similarly, although each illustrative embodiment listed above may directly depend on only one other illustrative embodiment, the disclosure includes each illustrative embodiment in combination with every other illustrative embodiment in the set of illustrative embodiments for the inventive concepts disclosed herein.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. An apparatus for imposing electric fields through a target region in a body of a patient, the apparatus comprising:
at least one transducer array having a plurality of electrode elements configured for placement on the body of the patient, the electrode elements configured to provide TTFields; and
a connector electrically connected to the at least one transducer array, wherein the connector comprises a first portion and a second portion, the first portion having a first plurality of conductive elements and at least one indicator electrical connector, the second portion having a second plurality of conductive elements, the first plurality of conductive elements and the at least one indicator electrical connector configured to mate with the second plurality of conductive elements, and has at least one associated monitoring circuit configured to provide feedback related to a status of the connector, the at least one associated monitoring circuit connected to the at least one indicator electrical connector configured to disconnect from the second plurality of conductive elements of the second portion at a first position relative to the second plurality of conductive elements and wherein the first plurality of conductive elements is configured to disconnect from the second plurality of conductive elements of the second portion at a second position relative to the second plurality of conductive elements, the second position being different from the first position.

2. The apparatus of claim 1, wherein the first plurality of conductive elements of the connector comprises a plurality of pins or socket connectors in electrical communication with the transducer array.

3. The apparatus of claim 2,
wherein the at least one indicator electrical connector includes an indicator pin integrated into the first portion of the connector; and
wherein the second plurality of conductive elements include an indicator socket connector associated with the indicator pin, the indicator socket connector integrated into the second portion of the connector.

4. The apparatus of claim 3, wherein the first plurality of conductive elements of the connector comprise a plurality of pins integrated into the first portion of the connector and wherein the second portion of the connector further includes a plurality of socket connectors wherein each socket connector is operable to receive a particular one of the plurality of pins integrated into the first portion of the connector.

5. The apparatus of claim 3, wherein a first length of at least one of the plurality of pins is greater than a second length of the indicator pin.

6. The apparatus of claim 4, wherein a first depth of the plurality of socket connectors is greater than a second depth of the indicator socket connector.

7. The apparatus of claim 6, wherein the connector further includes a first end and a second end with the indicator pin positioned at the first end of the connector.

8. The apparatus of claim 3, further comprising at least one resistor in electrical communication with the indicator socket connector, wherein feedback related to the status of the connector includes voltage changes at the at least one resistor.

9. The apparatus of claim 3, wherein the at least one indicator electrical connector includes at least two indicator pins, and wherein the connector comprises a first end, and a second end, wherein at least one indicator pin is positioned at the first end of the connector and at least one indicator pin is positioned at the second end of the connector.

10. The apparatus of claim 9, further comprising a conductive line positioned between at least two indicator socket connectors forming a monitoring circuit.

11. The apparatus of claim 10, wherein a controller is configured to determine the status of the connector via the monitoring circuit.

12. The apparatus of claim 11, wherein the controller determines the status of the connector by monitoring changes to current within the monitoring circuit or by monitoring changes to voltage within the monitoring circuit.

13. The apparatus of claim 1, wherein the at least one associated monitoring circuit is configured to generate a signal indicative of the status of the connector, and further comprising an indicator system configured to receive the signal and provide at least one of visual, auditory or haptic feedback to a user on the status of the connector.

14. The apparatus of claim 1, further comprising an electric field generator, wherein the connector includes the first portion configured to be connected to the second portion, and wherein the status of the connector is "disconnection" or "partial disconnection" of the first portion from the second portion, and wherein the at least one associated monitoring circuit is configured to generate a signal indicative of the status of the connector of "disconnection" or "partial disconnection" of the first portion and the second portion, and further wherein the electric field generator receives a signal that indicates the status of the connector of "disconnection" or "partial disconnection" of the first portion and the second portion and powers down the electric field generator.

15. A method for monitoring an apparatus for imposing electric fields through a target region in a body of a patient, the method comprising:
    electrically connecting a connector to at least one transducer array, wherein the at least one transducer array has a plurality of electrode elements configured for placement on the body of the patient, the electrode elements configured to provide TTFields;
    circulating current through at least one indicator pin integrated into a first portion of the connector, and through an associated indicator socket connector integrated into a second portion of the connector, wherein the at least one indicator pin has a first length and the first portion of the connector comprises a plurality of pins having a second length greater than the first length;
    monitoring data from the circulating current;
    determining status of the connector based on the monitored data; and,
    providing a predetermined action based on the status of the connector.

16. The method of claim 15, wherein the predetermined action is providing at least one of visual indicator, auditory indicator, or haptic indicator of the status of the connector to a user.

17. The method of claim 15, wherein the connector is configured to be connected to an electric field generator, and wherein the status of the connector is "disconnection" or "partial disconnection" of the at least one indicator pin from an associated indicator socket connector, and wherein the predetermined action is powering down the electric field generator.

18. A system comprising:
    a plurality of transducer arrays each having substrate supporting a plurality of electrode elements configured for placement on a body of a patient, the electrode elements configured to provide TTFields and at least one electrode element associated with a temperature sensor; each transducer array electrically connected to a first portion of a connector, and each transducer array comprising a distal circuit electrically coupled to each of the plurality of electrode elements of the transducer array and operable to receive a temperature signal from each of the associated temperature sensors and operable to output a DATA signal and to receive a TTField Signal, the distal circuit being either supported by the substrate, or integrated into the first portion of the connector, or both, or positioned in a circuit between the transducer array and the connector, the connector further comprising a plurality of pins or socket connectors having a first length in electrical communication with the transducer array; and, at least one monitoring circuit configured to provide feedback related to a status of the connector, the connector further comprising at least one indicator electrical connector with a second length less than the first length;
    a hub electrically coupled to each of the plurality of transducer arrays by a second portion of the connector configured to mate with the first portion of the connector; and
    an electric field generator electrically coupled to the hub and operable to receive one or more DATA signal and output one or more TTField Signal.

19. The system of claim 18, wherein the connector further comprises a first end and a second end; and wherein the monitoring circuit is coupled to the at least one indicator electrical connector comprising a first indicator pin and a second indicator pin, the first indicator pin positioned at the first end of the connector and the second indicator pin positioned at the second end of the connector; the connector further comprising a conductive line positioned between at least two indicator socket connectors forming the monitoring circuit configured to determine the status of the connector.

20. The system of claim 18, wherein the monitoring circuit generates a signal indicative of the status of the connector of "disconnection" or "partial disconnection" of the first portion and the second portion, and wherein the electric field generator receives a signal that indicates the status of the connector of "disconnection" or "partial disconnection" of the first portion and the second portion and powers down the electric field generator.

* * * * *